(12) United States Patent
Mukai et al.

(10) Patent No.: US 7,893,199 B2
(45) Date of Patent: Feb. 22, 2011

(54) PEPTIDES HAVING NEUTROPHIL-STIMULATING ACTIVITY

(75) Inventors: Hidehito Mukai, Tokyo (JP); Kaori Wakamatsu, Gunma (JP)

(73) Assignee: National University Corporation Gunma University, Gunma (JP)

( * ) Notice: Subject to any disclaimer, the term of this patent is extended or adjusted under 35 U.S.C. 154(b) by 31 days.

(21) Appl. No.: 12/443,404

(22) PCT Filed: Sep. 28, 2007

(86) PCT No.: PCT/JP2007/068970

§ 371 (c)(1),
(2), (4) Date: Mar. 27, 2009

(87) PCT Pub. No.: WO2008/038766

PCT Pub. Date: Apr. 3, 2008

(65) Prior Publication Data

US 2010/0009452 A1    Jan. 14, 2010

(30) Foreign Application Priority Data

Sep. 29, 2006   (JP)   .............................. 2006-267559

(51) Int. Cl.
*A61K 38/00* (2006.01)
*A61K 38/04* (2006.01)
*A61K 38/16* (2006.01)
*A61K 39/00* (2006.01)

(52) U.S. Cl. ........................ 530/300; 530/326; 530/324; 424/185.1; 424/198.1

(58) Field of Classification Search ........................ None
See application file for complete search history.

(56) References Cited

U.S. PATENT DOCUMENTS

| | | | |
|---|---|---|---|
| 7,067,624 | B2 | 6/2006 | Manners et al. |
| 7,169,565 | B2 * | 1/2007 | Ruben et al. .................. 435/7.1 |
| 7,285,618 | B1 | 10/2007 | Mukai et al. |
| 2005/0147993 | A1 | 7/2005 | Khan |
| 2006/0121498 | A1 | 6/2006 | Murphy et al. |
| 2006/0211647 | A1 | 9/2006 | Khan |
| 2006/0217891 | A1 | 9/2006 | Tanuma et al. |

FOREIGN PATENT DOCUMENTS

| | | |
|---|---|---|
| EP | 1 295 943 | 3/2003 |
| JP | 2001-510995 | 8/2001 |
| JP | 2004-081178 | 3/2004 |
| WO | WO 01/66734 | 9/2001 |
| WO | WO 2004/078783 | 9/2004 |

OTHER PUBLICATIONS

PCT/JP2007/068970 International Search Report dated Oct. 30, 2007.

Mukai, H., et al., "Investigation on mechanism of onset of inflammation caused by new-type neutrophil-activating peptide", *Seikagaku*, 2000, vol. 72, No. 8, p. 909, 2P-391 (Full English translation provided).

Mukai, H., et al., "Identification of neutrophil-activating factors and analysis of these functions, in association with 'second function' of proteins", *Seikagaku*, 2001, vol. 73, No. 8, p. 1009, 4P-399 (Full English translation provided).

Mukai, H., et al., "Investigation on action mechanism of novel neutrophil-activating peptides", *Seikagaku*, 2002, vol. 74, No. 8, p. 764, 2P-328 (Full English translation provided).

Ueki, N., et al., "Cryptic functional peptides—systematic identification and novel biological signaling system, accumulative signaling", *Kagaku to Seibutsu*, 2006, vol. 44, No. 11, pp. 728-730 (Partial English translation provided).

PCT/JP2007/068970 Translation of International Preliminary Report on Patentability dated May 22, 2009.

Bataille, D., et al., "The Biological Significance of 'Enteroglucagon'. Present Status", *Peptides*, 1986, vol. 7, Suppl. 1, pp. 37-42.

Green, Douglas R., "Apoptotic pathways: ten minutes to dead", *Cell*, 2005, vol. 121, pp. 671-674.

Higashijima, Tsutomu, et al., "Mastoparan, a peptide toxin from wasp venom, mimics receptors by activating GTP-binding regulatory proteins (G proteins)", *The Journal of Biological Chemistry*, 1988, vol. 263, No. 14, pp. 6491-6494.

Higashijima, Tsutomu, et al., "Regulation of $G_i$ and $G_o$ by Mastoparan, related amphiphilic peptides, and hydrophobic amines", *The Journal of Biological Chemistry*, 1990, vol. 265, No. 24, pp. 14176-14186.

Mukai, H., "Attempt to identify new substance for biological regulation in association with 'second function' of proteins", *Peptide Newsletter Japan*, 2001, No. 41, pp. 1-2. (Full English translation provided).

Mukai, H., et al., "Novel classes of neutrophil-activating peptides: isolation and their physiological significance", *Peptides: The wave of the future*, 2001, pp. 1014-1015.

Mukai, H., et al., "Novel neutrophil-activating peptides: physiological roles of direct activation of GTP-binding regulatory proteins by these peptides", *Peptide Revolution: Genomics, Proteomics & Therapeutics*, 2003, pp. 553-555.

Nakajima, T., et al., "Mastoparan as a G Protein Activator", Method and tools in bioscience and medicine, *Animal Toxins*, 2000, pp. 116-125.

* cited by examiner

*Primary Examiner* — Robert Landsman
*Assistant Examiner* — Bruce D Hissong
(74) *Attorney, Agent, or Firm* — Kilpatrick Stockton LLP

(57) ABSTRACT

A peptide having a sequence which satisfies all of the following requirements (I) to (V) and has an activity of stimulating an immune cell: (I) the number of constituent amino acid residues is 12 to 36; (II) the sequence is amphipathic; (III) the charge of the whole molecule is +2 or more; (IV) when constituent amino acid residues are arranged so as to form an a-helical structure, a side chain of any aromatic amino acid residue is not located between side chains of at least two positively charged amino acid residues on a side where hydrophilic amino acid residues are located; and (V) the sequence contains an amino acid residue which serves as a cleavage point for a mitochondrial processing enzyme.

2 Claims, 12 Drawing Sheets

[Fig.1]
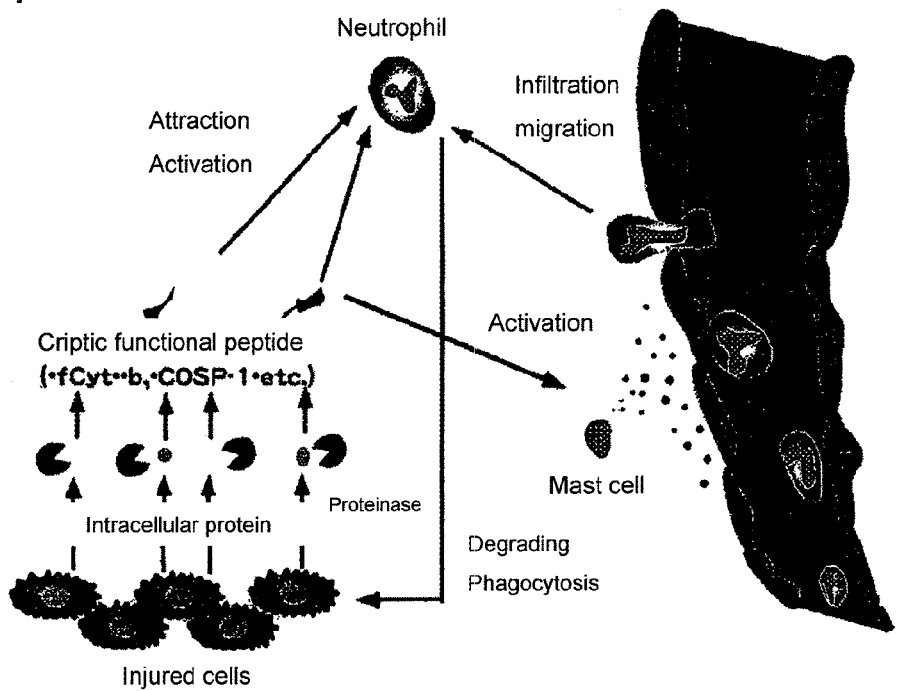
[Fig.2]
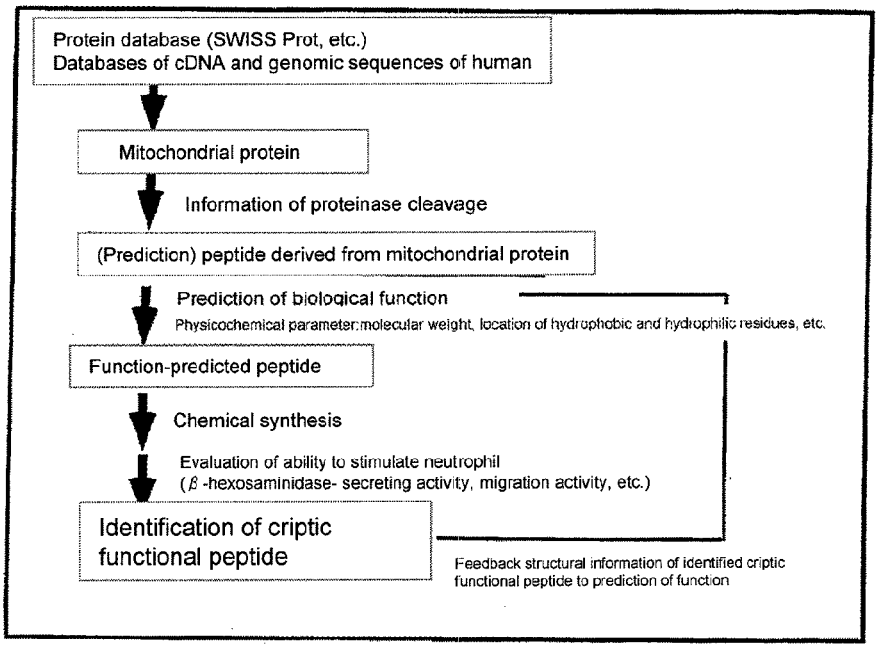

[Fig. 3]
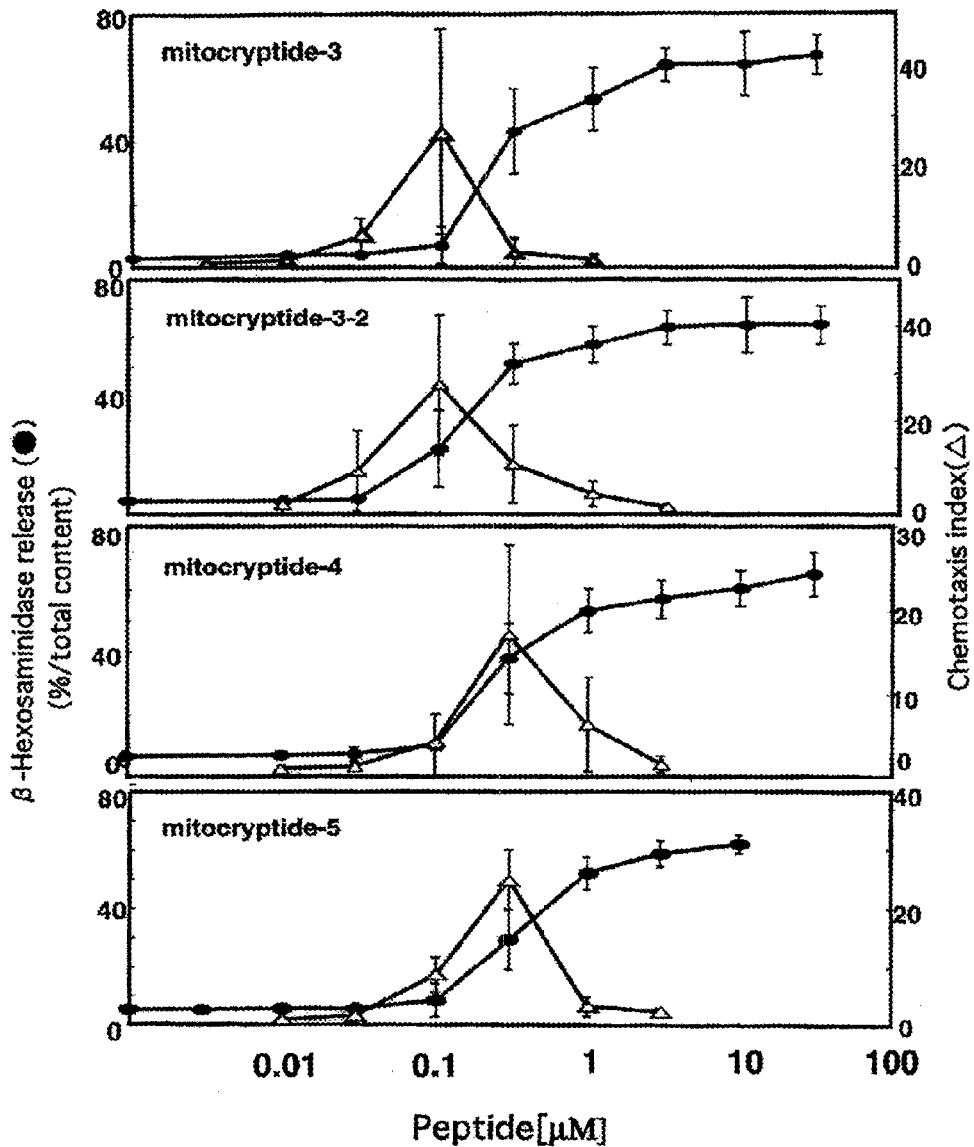

[Fig. 4]
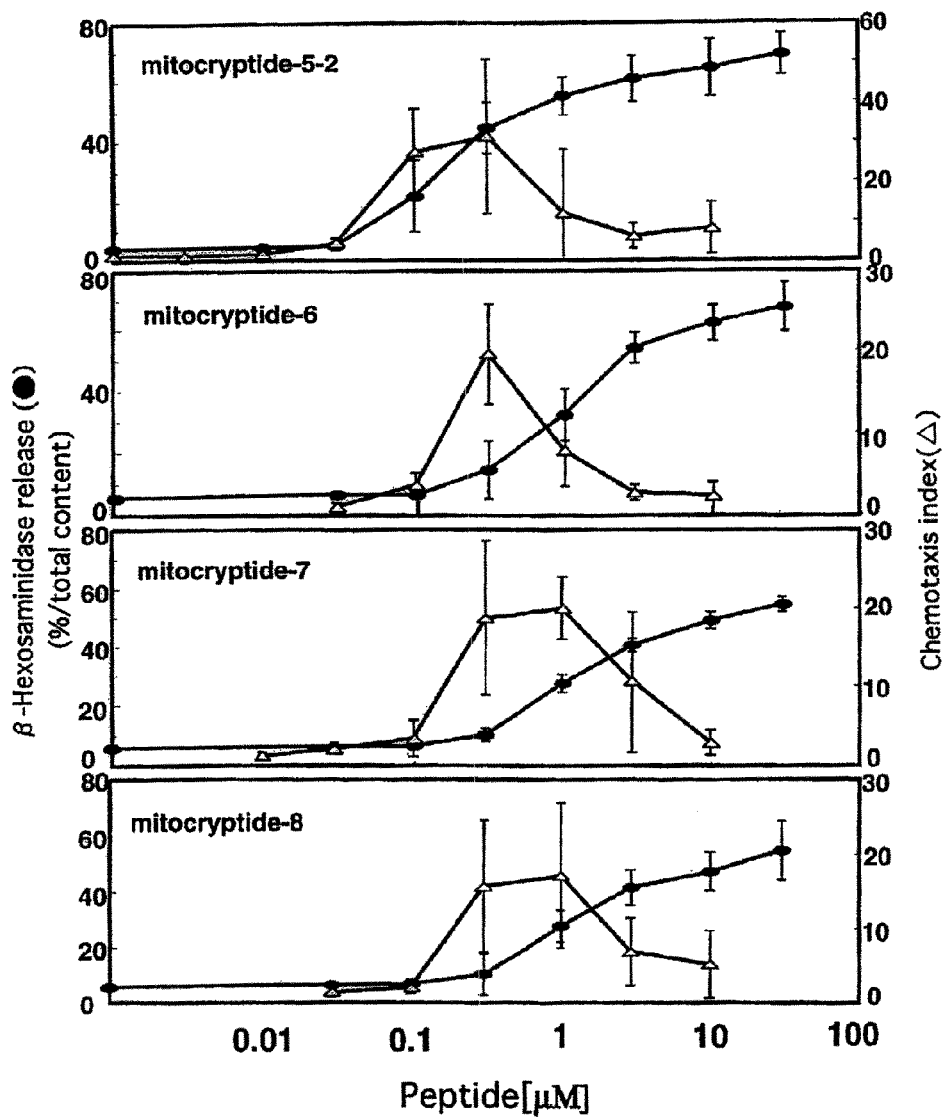

[Fig. 5]
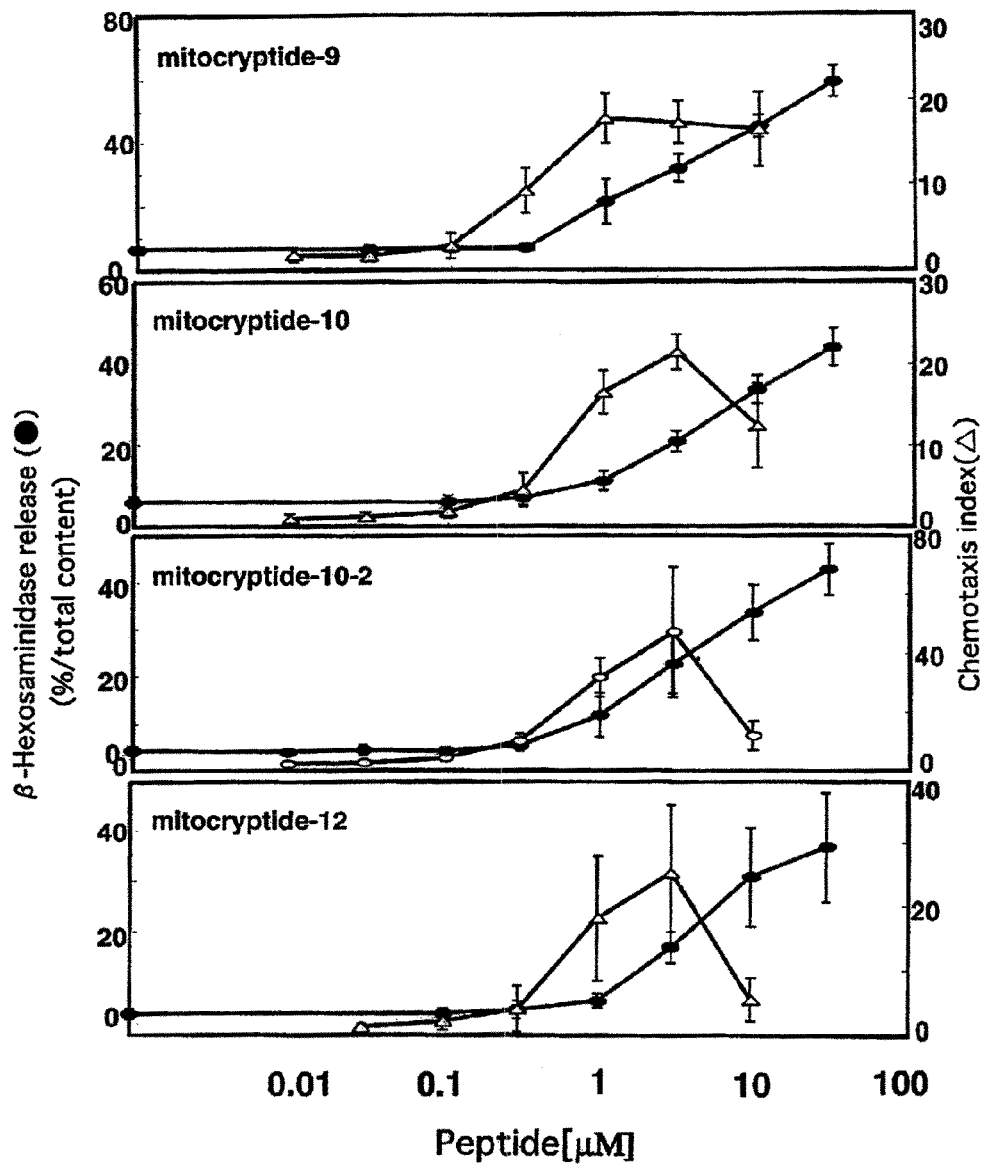

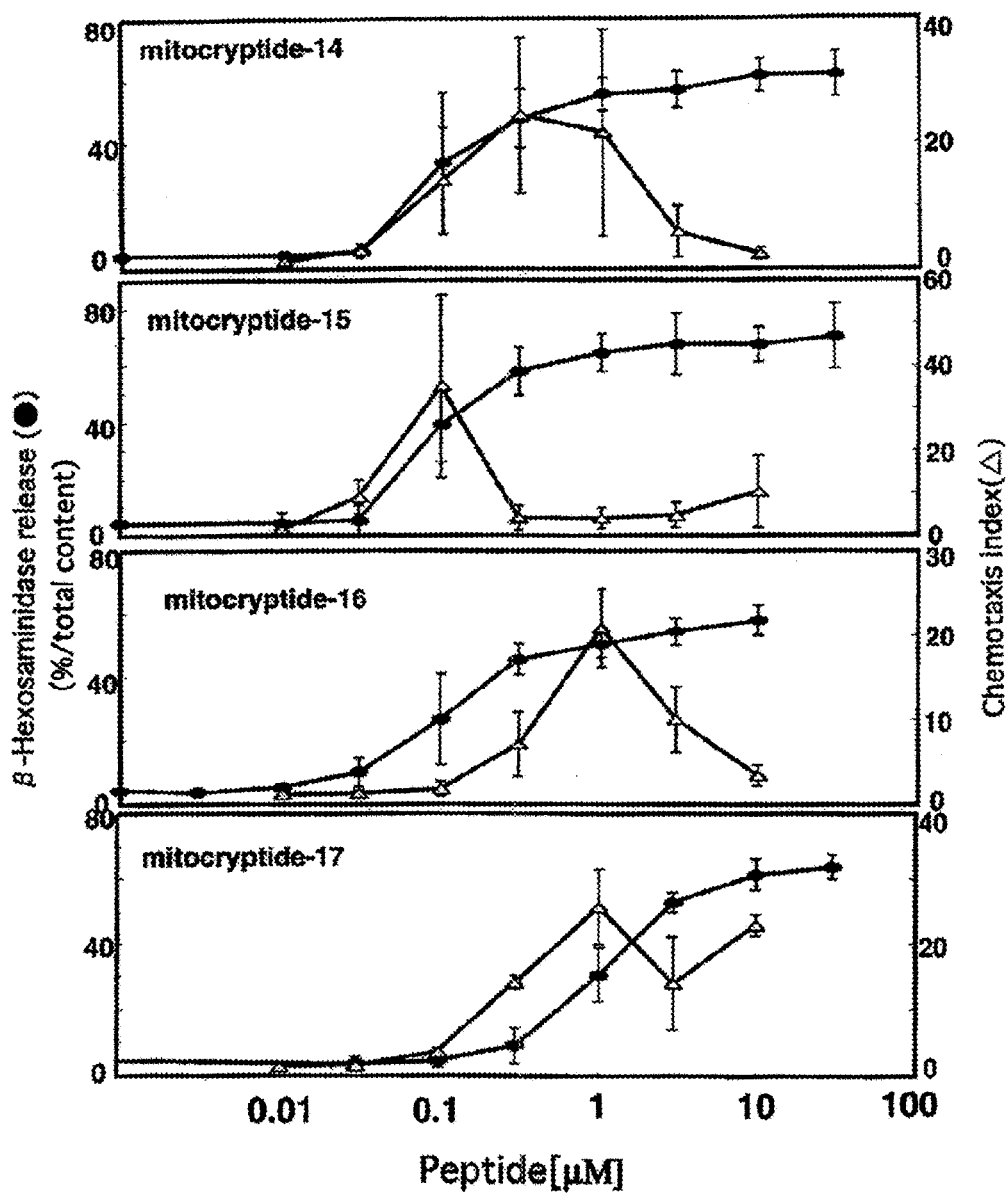
[Fig. 6]

[Fig. 7]
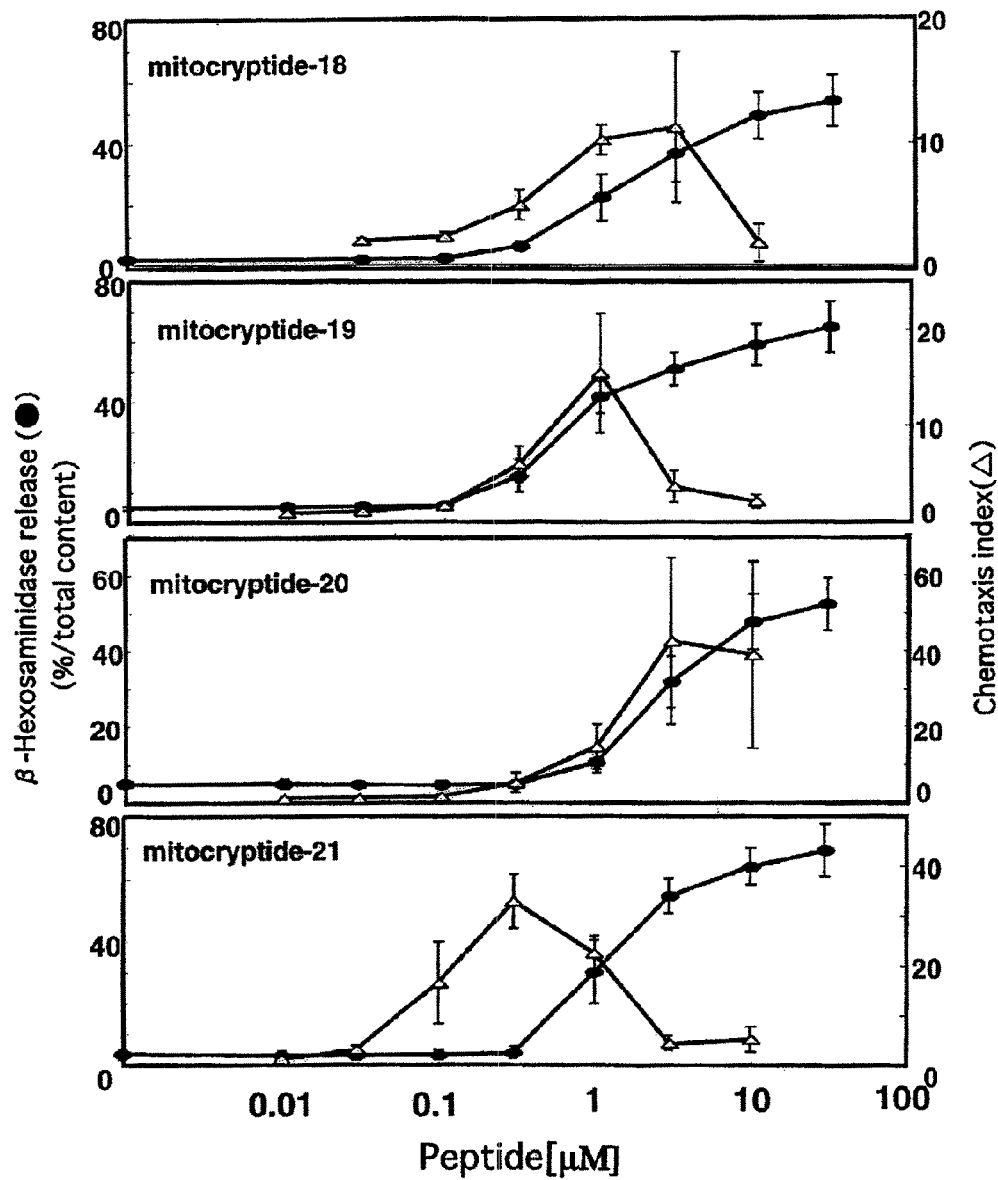

[Fig. 8]
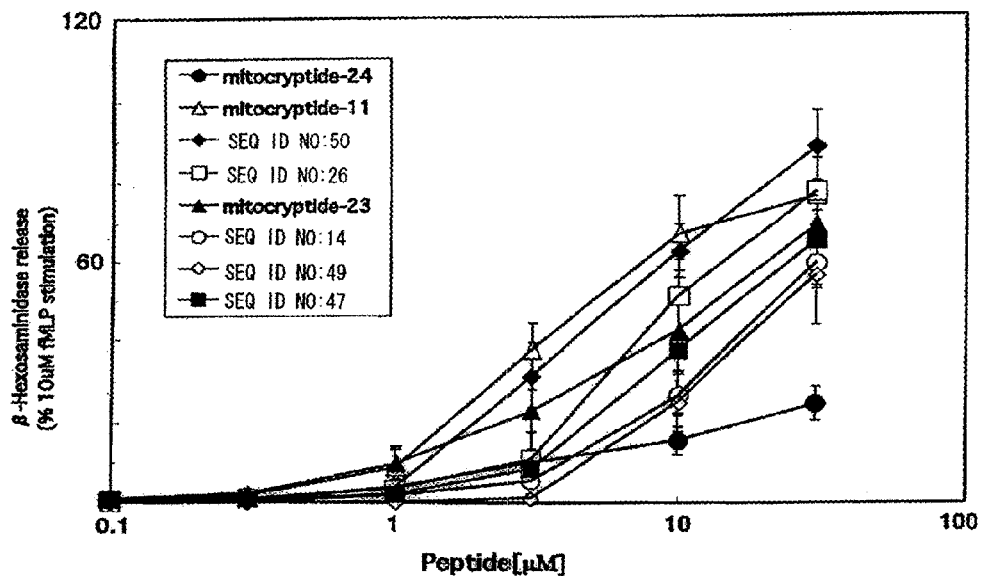
[Fig. 9]
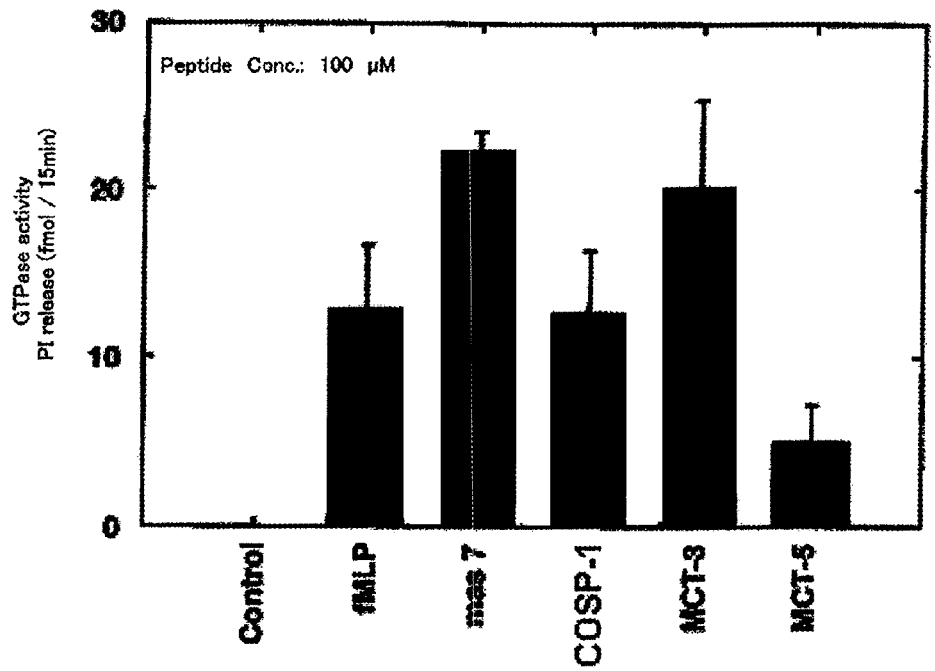

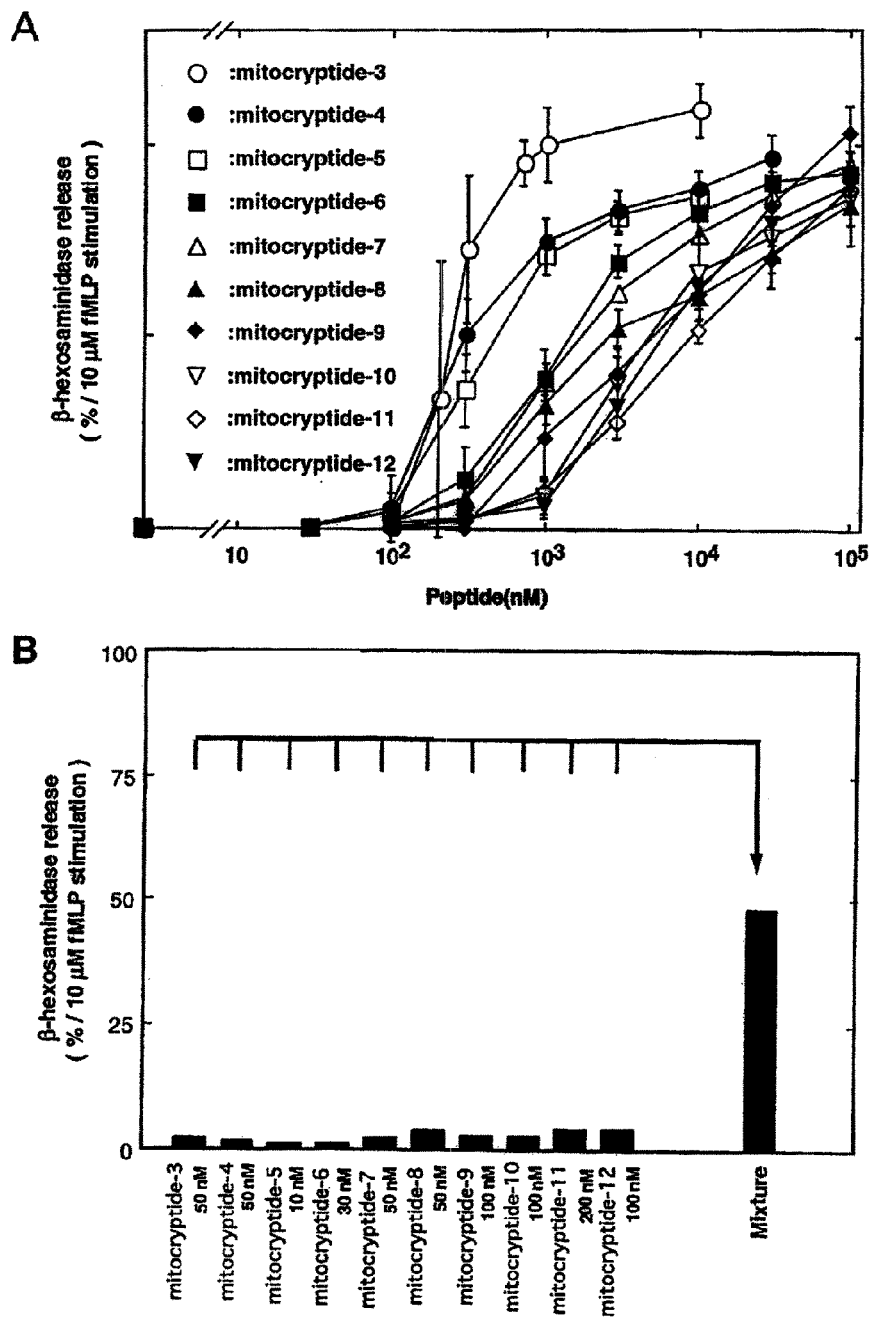
[Fig. 10]

[Fig.11 A]
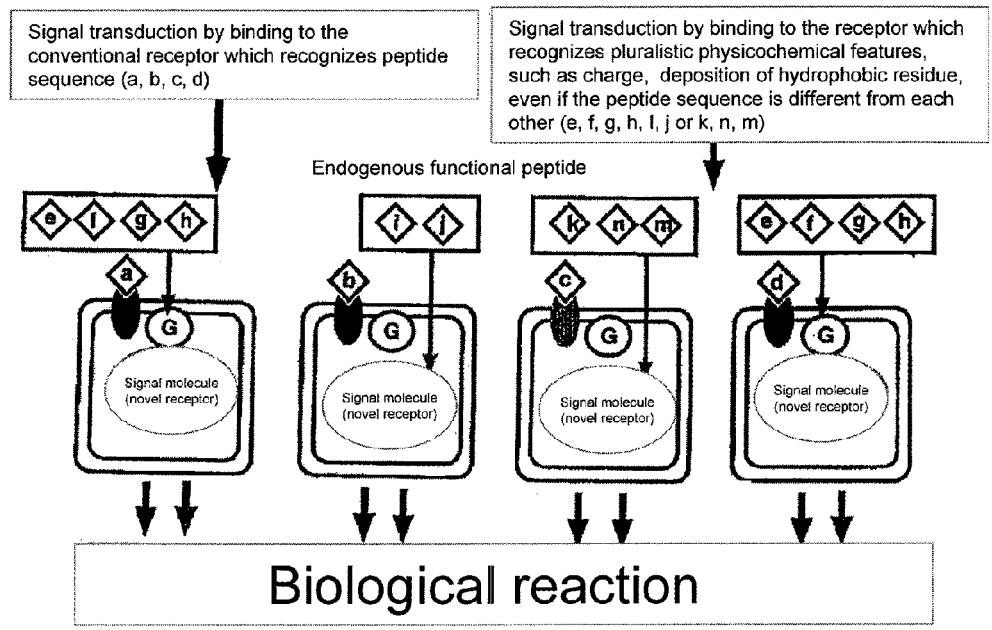
[Fig.11 B]
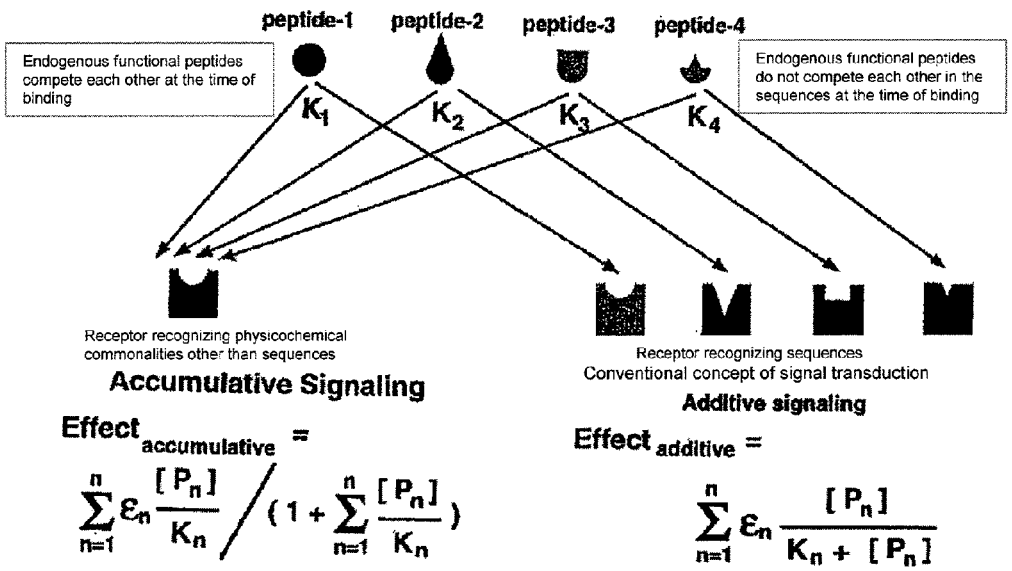

[Fig. 12]
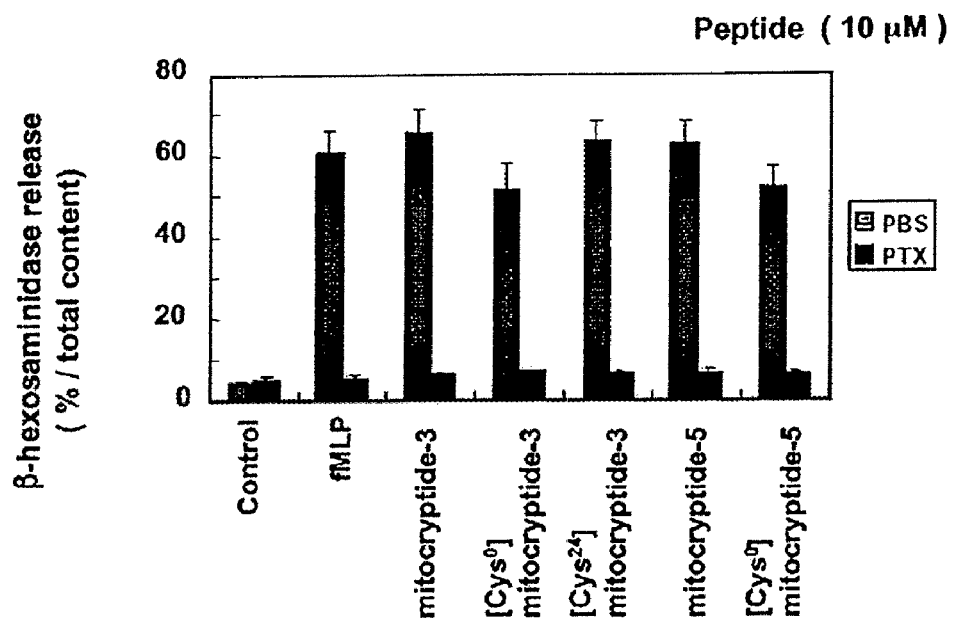

[Fig. 13A]
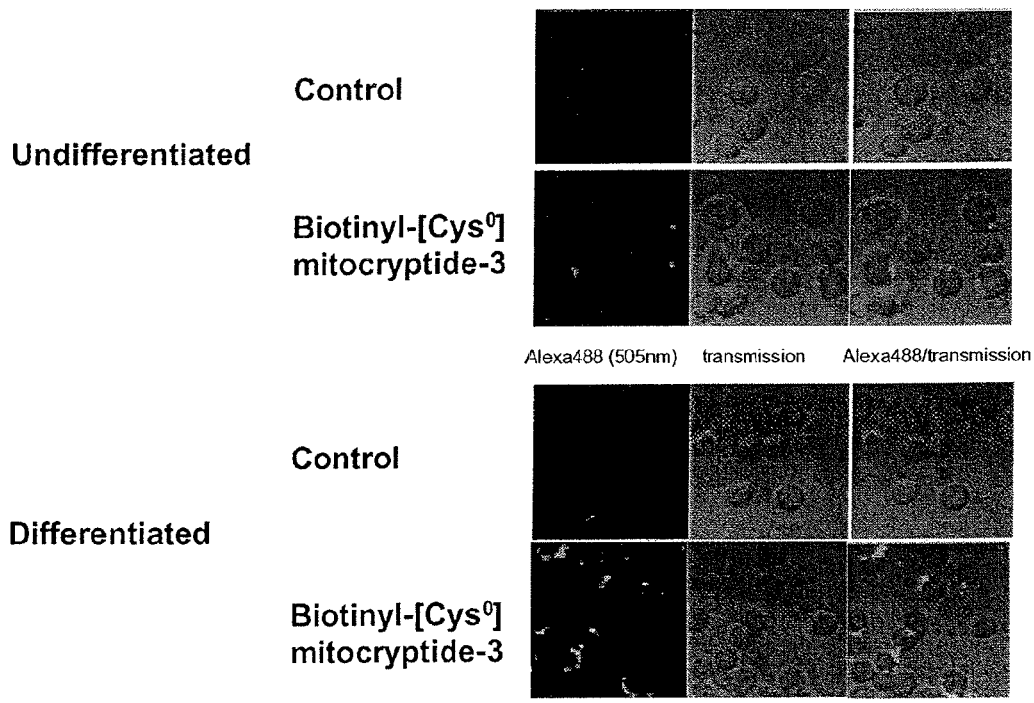
[Fig. 13B]
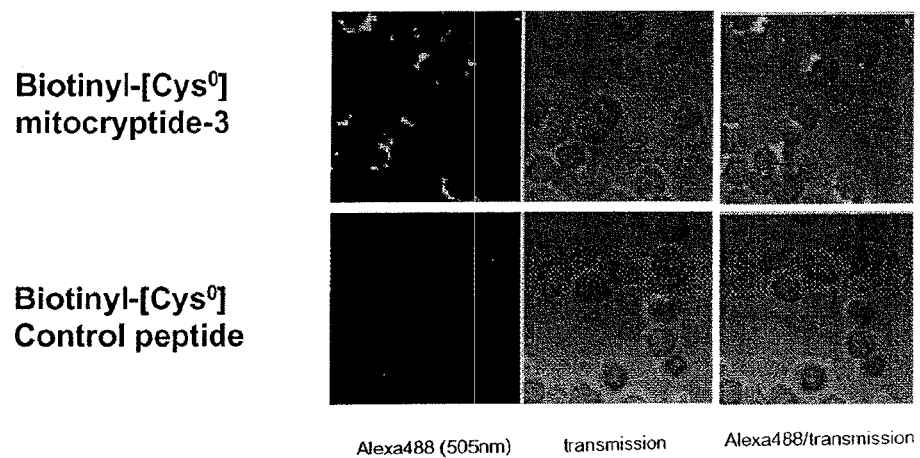

[Fig. 14]
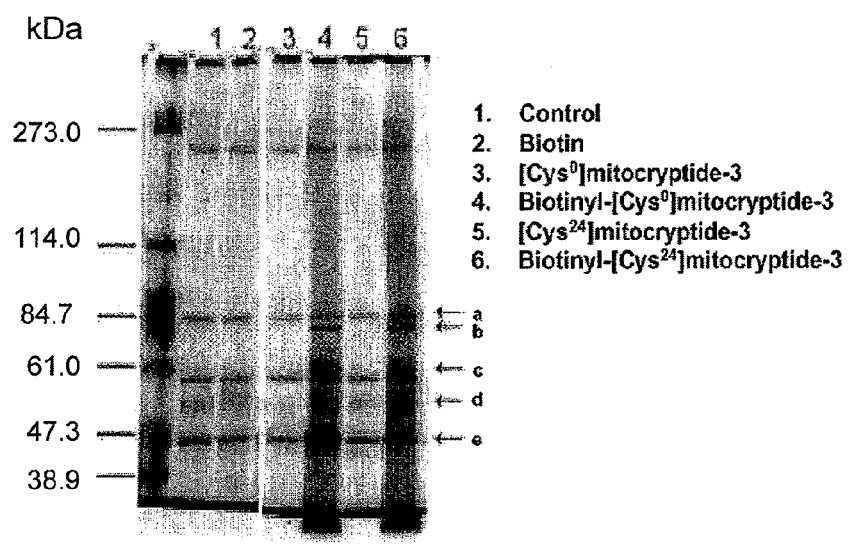
1. Control
2. Biotin
3. [Cys$^0$]mitocryptide-3
4. Biotinyl-[Cys$^0$]mitocryptide-3
5. [Cys$^{24}$]mitocryptide-3
6. Biotinyl-[Cys$^{24}$]mitocryptide-3
[Fig. 15]
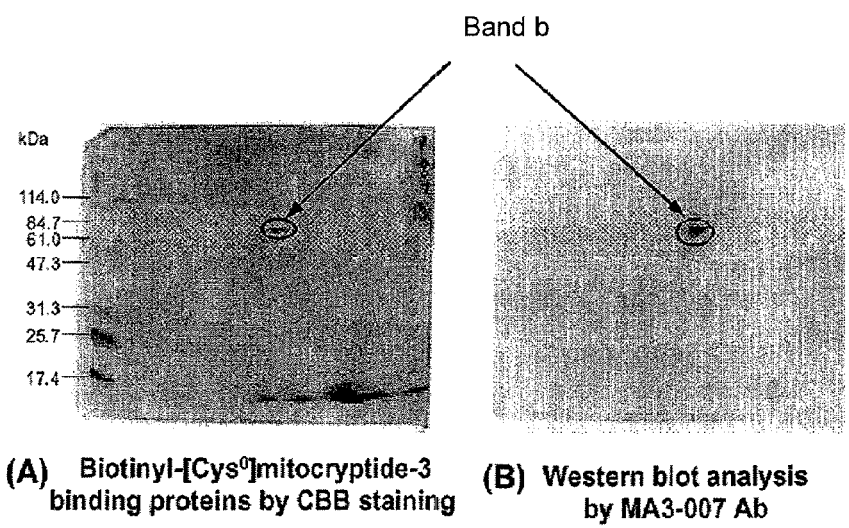
(A) Biotinyl-[Cys$^0$]mitocryptide-3 binding proteins by CBB staining
(B) Western blot analysis by MA3-007 Ab
( 1st, pH 3-10; 2nd, 5-20 % gel )

PEPTIDES HAVING NEUTROPHIL-STIMULATING ACTIVITY

PRIOR RELATED APPLICATIONS

The present application is a 35 U.S.C. §371 National Phase filing of PCT Application No. PCT/JP2007/068970, filed Sep. 28, 2007, which claims priority to Japanese Patent Application No. 2006-267559, filed Sep. 29, 2006, each of which is incorporated by reference in its entirety.

TECHNICAL FIELD

The present invention relates to a peptide having a function of stimulating (migrating and activating) an immune cell, such as a neutrophil, and use thereof. The functional peptide of the present invention, a receptor of the peptide, and antibodies to the peptide and the receptor can be applied for treating, diagnosing, and preventing a disease or state involved in the immune cell.

BACKGROUND ART

An organism maintains its "life" by exchanging much information to each other among the constituent tissues or cells. The exchange of information is mediated by chemical substances such as a neurotransmitter, a hormone, and a cytokine, particularly a large number of peptide factors. Therefore, many endogenous regulatory peptides have been extracted from organisms and subjected to structure determination, and their functions have been clarified. However, almost all these functional peptides have no function only by being translated to proteins from the genes, and hence, there is no way but to search the peptide by purifying the peptide from an organism and evaluating its function. Therefore, a large number of unidentified functional peptides may exist. In addition, if the function is identified once, a search for another role that the peptide may have is not attempted (Non-patent Document 1).

However, because the fact that cytocrome c, which has been known as a protein involved in the mitochondrial electron transport chain for a long time, transfers from the mitochondria to a cytoplasm to induce the apoptosis (programmed cell death) of the cell has been accidentally found recently (Non-patent Document 2), the inventors of the present invention considers that many proteins and peptides other than cytochrome c probably have quite-different multiple biological functions. Further, as described above, many biological regulatory peptides are subjected to various limited proteolysis and converted into matured peptides after being transcribed and translated from the genes, and in this time, many fragment of peptides are produced simultaneously. In general, it is widely considered that these peptides are produced as by-products in order to produce intended biological regulatory peptides and have no function in themselves. However, there is no foundation in the view at all, and for example, actually, the function of glucagon-like peptide 1 which was generated at the same time as glucagon was produced was accidentally identified (Non-patent Document 3). The inventors of the present invention conceive that many peptides generated by cleavage of the proteins are involved in many homeostatic mechanisms and signal transductions of organisms that have yet to be clarified. Actually, the inventors have discovered recently that many endogenous functional peptides generated by cleavage of the protein may be involved in a mechanism of defending the organism (Patent Document 1 and Non-patent Document 1).

The mammalian has complicate, exquisite defense mechanisms called immune system, to thereby prevent entering bacteria and viruses from outside and process foreign substances taken into the organisms (Non-patent Document 4).

The immunoreaction in individuals are classified into a natural immunity in which the immunity can response immediately but recognition of the immunity is ambiguous, and acquired immunity in which the recognition of the immunity is specific (Non-patent Document 4). In the natural immunity system, foreign substances that enter the body are rapidly processed by the involvement of a neutrophil, a macrophage, the complement system, or the like. On the other hand, in the acquired immunity, a lymphocyte plays an important role. That is, when the lymphocyte recognizes a foreign substance once, the substance is memorized by the lymphocyte forever, thereby, when the lymphocyte meets the same substance again even after a long period, the immunity reacts more strongly and treats more rapidly than the case of elimination only by the natural immunity. Thus, the immune system establishes the defense mechanism in which the immunity starts from the natural immunity with less specific recognition and transfers to the acquired immunity with more specific recognition (Non-patent Document 4).

In the natural immunity, there is the neutrophil as a leukocyte that plays an important role at first (Non-patent Documents 4 and 5). As the main function of the neutrophil, a defense reaction to the invasion of foreign substances and microorganisms is mentioned. That is, when a microorganism invades the body, the neutrophil passes the blood vessel wall and infiltrates the bacterial nest to exhibit phagocytosis and disinfection abilities, thereby playing its role (Non-patent Document 5). Thus, the infiltration of the neutrophil to the tissue aims at eliminating the foreign substances and repairing the tissues for the organism. However, if these reactions become excessive, the elimination of the foreign substances leads to the destruction of the tissues, and there may be such a danger as a precipitating factor that the destruction of the tissues leads to the myocardial infarction and the organ dysfunction. From the foregoing, the infiltration of the neutrophil to the tissues is likened to "sword with a double edge" having two aspects (Non-patent Document 5).

As a chemotactic factor causing the infiltration of the neutrophil, there is known a protein factor called chemokine in addition to fMLP, leukotriene $B_4$, completion component C5a, and the like (Non-patent Documents 5 and 6). The name of the chemokine is derived from "chemotaxis cytokine" and is a general name of the protein molecule group having the ability of migrating or activating a leukocyte. These are classified into four kinds of subfamilies, CXC, CC, C, and $CX_3C$ according to the positional relationship of the Cys residue preserved in the primary structure of the protein (Non-patent Document 6). Of these, the chemokine in which an amino acid residue is inserted between two Cys residues is the CXC subfamily. The typical CXC subfamily is interleukin 8 (IL-8) and the like and these chemokines mainly target the neutrophil (Non-patent Document 6). However, these chemokines are rarely present in general tissues and known as factors synthesized and produced by transcription and translation of the genes after generation of inflammation. However, because the infiltration of the neutrophil is confirmed several minutes after the tissue injury is generated, the rapid infiltration of the neutrophil may not be probably induced by the chemokine.

Then, the inventors attempted the identification of the factor activating the neutrophil, the presence of the factor being predicted but having yet to be identified, by extracting and purifying the factor from the heart where a large amount of the neutrophil are known to infiltrate at the time of ischemia-reperfusion injury. As a result, two kinds of peptide activation factors, i.e., COSP-1 and fCytb have been identified until the present, but these are peptides derived from the mitochondrial protein (Non-patent Document 7 and Patent Document 1). In addition, the presence of a large number of neutrophil-activating factors derived from the mitochondrial protein other than the COSP-1 and fcytb has been clarified simultaneously. Thus, it has been considered that organisms have novel defense mechanisms involved in these factors (Non-patent Documents 7 and 8 and Patent Document 1). That is, when an accidental damage occurs on cells and the cells are killed, the mitochondria in the cells inflates and mitochondrial proteins are released outside the cells. Then, the mitochondrial proteins released are specifically cleaved by a protease such as trypsin and become activation peptides having functions, such as the COSP-1 and fcytb. There may be a novel defense mechanism which processes substances derived from abnormal cells or dead cells, which become harmful substances, as the result that a large number of activation peptides obtaining functions by the cleavage with the protease induce and activate the neutrophil (FIG. 1). Thus, the presence of a large number of neutrophil-activating factors in the organism is clarified. In order to reveal the defense mechanism involved in these peptides and further clarify the actual situation of the disease such as the ischemia-reperfusion injury involved in the mechanism, it is essential to identify these peptides. However, if these peptides are identified by isolation and purification form organisms as are conventionally done, extremely much labor and time are required.

Patent Document 1: WO 01/066734, Hidehito Mukai, Yoshisuke Nishi, and Eisuke Munekata
Non-patent Document 1: Hidehito Mukai, Peptide News Letter, 41, 1-2, 2001
Non-patent Document 2: Green, D. R., Cell, 121, 671-674, 2005
Non-patent Document 3: Bataille, D., Jarrousse, C., Kervran, A., Depigny, C., and Dubrasquet, M., Peptides, 7, 37-42, 1986
Non-patent Document 4: Ivan Roitt, Jonathan Brostoff, David Male, Immunology illustrated, Nankodo Co., Ltd., 2000
Non-patent Document 5: Shigeki Mizukami, Leukocyte and biological defense, Kodansha Ltd., 1990
Non-patent Document 6: Yoshihiro Matsumoto, Koji Matsushima, Protein, Nucleic Acid, and Enzyme, 45, 979-984, 2000
Non-patent Document 7: Mukai, H., Hokari, Y., Seki, T., Nakano, H., Takao, T., Shimonishi, Y., Nishi, Y., and Munekata, E., Peptides: The Wave of the Future, 2001, 1014-1015, 2001
Non-patent Document 8: Mukai, H., Matsuo, Y., Kamijo, R., and Wakamatsu, K., Peptide Revolution: Genomics, Proteomics & Therapeutics, 2003, 553-555, 2004
Non-patent Document 9: Higashijima, T., Uzu, S., Nakajima, T., and Ross, E. M., The Journal of Biological Chemistry, 263, 6491-6494, 1988
Non-patent Document 10: Higashijima, T., Burnier, J., and Ross. E. M., The Journal of Biological Chemistry, 265, 14176-14186, 1990
Non-patent Document 11: Grant, G. A., Synthetic peptides-A user's guide, 2nd edition, Oxford University Press, 2002.
Non-patent Document 12: Nakajima, T., Wakamatsu, K., and Mukai, H., Methods and Tools in Biosciences and Medicine, Animal Toxins, Rochat, H., and Martin-Eauclaire, M.-F., eds. Birkhaeuser Verlag Basel, Switzerland, pp 116-125, 2000

DISCLOSURE OF THE INVENTION

The endogenous functional peptide generally becomes a matured peptide having an activity for the first time by cleavage after being translated as a protein, and hence, an expression cloning method which is often used for discovering the functions of proteins cannot be applied. Therefore, in current situation, in order to identify the endogenous peptide which is suggested to be present now in a large amount and activate an immune cell such as a neutrophil, there is only a method of determining the structure of the peptide chemically by extracting the peptide from a biological tissue.

The present invention has been completed in view of the circumstances. An object of the present invention is to provide: (1) efficient means for identifying a functional peptide; (2) a peptide activating an immune cell such as the neutrophil or a peptide which inhibits a receptor activation as a result of desensitization of the receptor of the peptide by activating the immune cell strongly; and (3) a method of cumulative administration of the functional peptide having a higher-order structure identical to that formed when the peptide binds to its receptor.

The inventors of the present invention have extensively studied to efficiently identify a large amount of factors activating an immune cell such as the neutrophil. As a result, the inventors have established a method of predicting a peptide sequence which has an activity and functions in an organism from a genome sequence and a protein database. Then, the peptide presumed to have the activity was actually synthesized chemically and its biological functions were evaluated, thereby 44 kinds of novel neutrophil-activating peptides were identified. Further, the proteins which may be receptors of these peptides were identified.

That is, the present invention is as follows.

[1] A peptide comprising a sequence satisfying all of the following requirements (I) to (V) and having an activity of stimulating an immune cell:

(I) the number of constituent amino acid residues is 12 to 36;

(II) the sequence is amphipathic;

(III) the charge of the whole molecule is +2 or more;

(IV) when constituent amino acid residues are arranged so as to form an α-helical structure, a side chain of any aromatic amino acid residue is not located between side chains of at least two positively charged amino acid residues on a side where hydrophilic amino acid residues are located; and (V) the sequence contains an amino acid residue which serves as a cleavage point for a mitochondrial processing enzyme.

[2] The peptide according to [1], wherein the immune cell is a neutrophil.

[3] The peptide according to [1] or [2], which is selected from the following items (a) and (b):

(a) a peptide consisting of the amino acid sequence of SEQ ID NO: 1, 2, 3, 4, 5, 7, 8, 9, 10, 11, 12, 13, 14, 15, 16, 18, 19, 22, 23, 24, 25, 26, 27, 28, 29, 31, 32, 33, 34, 35, 36, 37, 39, 40, 42, 43, 44, 45, 46, 47, 48, 49, 50, or 51; and (b) a peptide consisting of the amino acid sequence of SEQ ID NO: 1, 2, 3, 4, 5, 7, 8, 9, 10, 11, 12, 13, 14, 15, 16, 18, 19, 22, 23, 24, 25, 26, 27, 28, 29, 31, 32, 33, 34, 35, 36, 37, 39, 40, 42, 43, 44, 45, 46, 47, 48, 49, 50, or 51 in which one or several amino acids are deleted, substituted, inserted, or added, and having an activity of stimulating an immune cell.

[4] The peptide according to any one of [1] to [3], wherein a receptor of the peptide is a protein containing the amino acid sequence of SEQ ID NO: 52.

[5] An antibody to the peptide according to any one of [1] to [3].

[6] A method of diagnosing an immune cell related disease, comprising detecting the peptide according to any one of [1] to [3].

[7] The method according to [6], wherein the immune cell is a neutrophil.

[8] A method of searching a peptide having an activity of stimulating an immune cell, comprising searching a sequence satisfying all the following requirements (I) to (V) and measuring an activity of stimulating an immune cell of a peptide which has the sequence:

(I) the number of constituent amino acid residues is 12 to 36;

(II) the sequence is amphipathic;

(III) the charge of the whole molecule is +2 or more;

(IV) when constituent amino acid residues are arranged so as to form an α-helical structure, a side chain of any aromatic amino acid residue is not located between side chains of at least two positively charged amino acid residues on a side where hydrophilic amino acid residues are located; and (V) the sequence contains an amino acid residue which serves as a cleavage point for a mitochondrial processing enzyme.

BRIEF DESCRIPTION OF THE DRAWINGS

[FIG. 1] A schema of a defense mechanism in which a large amount of neutrophil-activating peptides are involved.

[FIG. 2] A procedure for predicting and identifying a functional peptide.

[FIG. 3] β-hexosaminidase-secreting activity and migration activity (1) of neutrophil-like differentiated HL-60 cells by predicted activation peptides.

[FIG. 4] β-hexosaminidase-secreting activity and migration activity (2) of neutrophil-like differentiated HL-60 cells by predicted activation peptides.

[FIG. 5] β-hexosaminidase-secreting activity and migration activity (3) of neutrophil-like differentiated HL-60 cells by predicted activation peptides.

[FIG. 6] β-hexosaminidase-secreting activity and migration activity (4) of neutrophil-like differentiated HL-60 cells by predicted activation peptides.

[FIG. 7] β-hexosaminidase-secreting activity and migration activity (5) of neutrophil-like differentiated HL-60 cells by predicted activation peptides.

[FIG. 8] β-hexosaminidase-secreting activity and migration activity (6) of neutrophil-like differentiated HL-60 cells by predicted activation peptides.

[FIG. 9] Activation of G protein in a membrane fraction of neutrophil-like differentiated HL-60 cells by predicted activation peptides. MCT-3: mitocryptide-3; MCT-5: mitocryptide-5

[FIGS. 10] Concentration dependency (A) of β-hexosaminidase-secreting activity by predicted activation peptides and concerted effect (B) by mixed stimulation.

[FIG. 11A] A schema of a novel signal transduction mechanism in an organism, "accumulative signaling": this figure illustrates a schema of a novel organism regulation mechanism "accumulative signaling", the presence of which has been indicated in the research of the present invention.

[FIG. 11B] A schema of a new signal transduction mechanism in an organism, "accumulative signaling": this figure illustrates a difference between an information transduction concept (additive signaling) by a conventional endogenous functional peptide and a concept of the accumulative signaling, the presence of which has been indicated in the research of the present invention.

[FIG. 12] β-hexosaminidase-secreting activity in HL-60 cells by predicted activation peptides and their derivative peptides used in a experiment of receptor identification, and an inhibition effect of pertussis toxin (PTX) on the stimulation activities of these peptides. PBS refers to the results of stimulation by respective peptides after a pretreatment for 16 hours with addition of PBS to the cells. PTX refers to the results of stimulation by respective peptides after a pretreatment for 16 hours with addition of 50 ng/ml PTX to the cells.

[FIG. 13A] Binding between a derivative of a predicted activation peptide, and an undifferentiated HL-60 cell or a neutrophil-like differentiated HL-60 cell. The upper two sections illustrate the results of the undifferentiated HL-60 cell, and the lower two sections illustrate the results of the neutrophil-like differentiated HL-60 cell. The control refers to a case where no peptide is added. In addition, from the left, a fluorescence image of Alexa 488, an optical image of Alexa 488, and a superimposed image of Alexa 488 of both images are illustrated.

[FIG. 13B] Binding between a derivative of a predicted activation peptide or a control peptide having no activity, and a neutrophil-like HL-60 cell. From the left, a fluorescence image of Alexa 488, an optical image of Alexa 488, and a superimposed image of both images of Alexa 488 are illustrated.

[FIG. 14] Identification of a receptor protein of the predicted activation peptide by a one-dimensional SDS electrophoresis (a to e refer to specific binding proteins).

[FIG. 15] Identification of the receptor protein of the predicted activation peptide by a two-dimensional electrophoresis. The arrows indicate spots corresponding to the band b in FIG. 14. (A): staining with coomassie brilliant blue, (B): western blotting analysis

DESCRIPTION OF THE PREFERRED EMBODIMENTS

The peptide of the present invention has a sequence satisfying the following requirements (I) to (V) and has an activity of stimulating an immune cell (excluding COSP-1 itself).

(I) The number of constituent amino acid residues is 12 to 36;

(II) the sequence is amphipathic;

(III) the charge of the whole molecule is +2 or more;

(IV) when constituent amino acid residues are arranged so as to form an α-helical structure, a side chain of any aromatic amino acid residue is not located between side chains of at least two positively charged amino acid residues on a side where hydrophilic amino acid residues are located; and (V) the sequence contains an amino acid residue which serves as a cleavage point for a mitochondrial processing enzyme.

The phrase "the sequence is amphipathic" means that the sequence may have both hydrophilic residues and hydrophobic residues. The sequence preferably has a part having amphipathic helical structure in which a hydrophobic (aliphatic or aromatic) amino acid residue is located at one side and a hydrophilic amino acid residue is located at the opposite side when the peptide sequence is plotted as a helical wheel from the N-terminal side (for example, can be plotted with commercially available Genetyx or the like).

The phrase "charge of the whole molecule is +2 or more" means that the total charge of the charged amino acids in the peptide molecule is +2 or more, and specifically, means that the value obtained by subtracting the total number of amino acids having negatively charged side chains (glutamate and aspartate) from the total number of the amino acids having positively charged side chains (lysine and arginine) is +2 or more. Note that, when the charge of the whole molecules is calculated, the positive charge of the amino group in the amino acid at the N-terminal and the negative charge of the carboxyl group in the amino acid at the C-terminal may be taken into consideration, but these charges are cancelled.

The phrase "when constituent amino acid residues are arranged so as to form an α-helical structure, a side chain of any aromatic amino acid residue is not located between side chains of at least two positively charged amino acid residues on a side where hydrophilic amino acid residues are located" means that, when the sequence of the peptide is plotted as a helical wheel with the Genetyx or the like, a side chain of any aromatic amino acid (tryptophan, tyrosine, and phenyl alanine) is not located between side chains of positively charged amino acids (lysine and arginine) distributed in a hydrophilic side. Further, when the constituent amino acids are located so as to have an α-helix structure, a side chain of any aliphatic amino acid selected from methionine, isoleucine, leucine, and valine is not preferably located as well between side chains of positively charged amino acids.

The phrase "the sequence contains an amino acid residue which serves as a cleavage point for a mitochondrial processing enzyme" means, for example, that the sequence contains a residue located prior to or next to a cleavage point in a sequence defined as "cleavage motif by a mitochondrial processing enzyme" in Swiss-Prot data base.

The peptide of the present invention, in addition to the above (I) to (IV), preferably has a positively charged amino acid residue on any one of 3rd or 4th residue, 7th or 8th residue, 10th or 11th residue, 14th or 15th residue, 18th residue, and 21st or 22nd residue based on the positively charged amino acid residue (including a positive charge at the amino terminal).

The peptide of the present invention is preferably a peptide derived from a mitochondrial protein.

As the peptide having properties described in the above (I) to (V), the following peptide (a) is exemplified.

(a) a peptide consisting of the amino acid sequence selected from the group consisting of SEQ ID NOS: 1, 2, 3, 4, 5, 7, 8, 9, 10, 11, 12, 13, 14, 15, 16, 18, 19, 22, 23, 24, 25, 26, 27, 28, 29, 31, 32, 33, 34, 35, 36, 37, 39, 40, 42, 43, 44, 45, 46, 47, 48, 49, 50, and 51.

In addition, the peptide may be a homologue of the peptide (a), that is, a peptide (b) having an activity of stimulating an immune cell and being consisting of the amino acid sequence of SEQ ID NO: 1, 2, 3, 4, 5, 7, 8, 9, 10, 11, 12, 13, 14, 15, 16, 18, 19, 22, 23, 24, 25, 26, 27, 28, 29, 31, 32, 33, 34, 35, 36, 37, 39, 40, 42, 43, 44, 45, 46, 47, 48, 49, 50, or 51, in which one or several amino acids are deleted, substituted, inserted, or added. Here, the term "one or several" means preferably 1 to 5, more preferably 1 to 3, and still more preferably 1 to 2.

Note that the amino acid sequence of the peptide (b) has identity of not less than 80%, preferably not less than 90%, more preferably not less than 95%, and particularly preferably not less than 98% with respect to the amino acid sequence prior to introduction of the deletion, substitution, insertion, or addition.

The peptide (b) may be a homologue peptide derived from an animal other than human or an artificially mutated peptide.

Of these sequences, the peptides of SEQ ID NOS: 7, 9, 11, 12, 15, 18, 19, 22, 23, 24, 25, 28, 31, 32, 33, 34, 35, 37, 40, 42, 43, 46, 48, and 51 are more preferred. The peptides of SEQ ID NO: 19 (mitocryptide-3), SEQ ID NO: 23 (mitocryptide-4), SEQ ID NO: 15 (mitocryptide-5), SEQ ID NO: 37 (mitocryptide-14), SEQ ID NO: 48 (mitocryptide-15), and SEQ ID NO: 51 (mitocryptide-16) are still more preferred.

Further, the peptide (a) or peptide (b) may have one or several amino acids modified as long as the activity of stimulating an immune cell is maintained. The modification may occur in N-terminal (amino group), C-terminal (carboxyl group), and the side chain of an amino acid other than the N-terminal and C-terminal. Examples of the modification include formylation, acetylation, or methylation at the N-terminal, and esterification or amidation at the C-terminal.

As the "immune cell", T cell, B cell, macrophage, NK cell, neutrophil, acidophil, basophil, and the like are exemplified. The neutrophil is preferred and the above peptides only have to have at least an activity of stimulating the neutrophil and may further have activities of stimulating other immune cells.

The term "neutrophil" in this description includes a neutrophil of an animal including the human and a neutrophil-like cell. As a specific example of the neutrophil-like cell, an HL-60 cell differentiated by dibutyric cyclic AMP treatment is given.

The term "an activity of stimulating an immune cell" refers to an activity of promoting the migration or the activation of an immune cell. The term "an activity of stimulating a neutrophil" refers to an activity of promoting the migration (referred to as "chemotaxis" in some cases) and/or the activity of a neutrophil or a neutrophil-like cell of an animal including human. The migration includes the infiltration to a tissue and the transference to a spot. The activation includes the production of active oxygen, the secretion of degrading enzyme (such as β-hexosaminidase: β-HA), the production of various cytokines and peroxide substances, and the phagocytosis. The activity of stimulating a neutrophil can be detected by measuring the chemotactic activity of the neutrophil, the release of active oxygen, the secretion amount of β-HA, or the increase of $Ca^{2+}$ concentration in the cells. In addition, in this description, the phrase "a peptide has an activity of stimulating a neutrophil" includes the case where the peptide has one of an activity of promoting the migration of the neutrophil and an activity of promoting the activation of the neutrophil and the case where the peptide has both activities.

As a specific method of evaluating the activity of stimulating a neutrophil, the following method is exemplified: a peptide is added to a suspension of an HL-60 cell differentiated into a neutrophil-like cell or a suspension of a human leukocyte to stimulate the cell; and the amount of a substance in the cell or supernatant (activation index substance, for example, β-HA), which is produced when the neutrophil is activated is measured. The evaluation can be easily performed by adding cytochalasin B and DNase at the time of the stimulation and measuring a β-HA activity in the supernatant. Here, when the peptide of the present invention is added to the HL-60 cell differentiated into a neutrophil-like cell, the concentration of the peptide, at which 30% or more β-HA of total β-HA amount in cells before the stimulation can be secreted, is preferably 100 μM or less, more preferably 10 μM or less, and particularly preferably 1 μM or less.

In addition, the activity of stimulating a neutrophil of the peptide of the present invention can be also evaluated by measuring the migration activity using an undifferentiated HL-60 cell or an HL-60 cell differentiated into a neutrophil-like cell. A method of measuring the migration activity is also well known to persons skilled in the art. As the peptide of the present invention, a peptide exhibiting a migration activity to a neutrophil but not exhibiting the migration activity to an undifferentiated cell is preferred. For example, a peptide not exhibiting a migration activity to an undifferentiated HL-60 cell but exhibiting the migration activity to a differentiated HL-60 cell is preferred.

The peptide of the present invention can be chemically synthesized. The synthesis can be performed using general means for a peptide synthesis, such as a Boc method, Fmoc method, and the like. In addition, the peptide of the present invention can be prepared from an animal tissue material such as a human culture cell. For the preparing operation, general means for purifying a peptide component from an animal tissue material (such as affinity chromatography, ion exchange chromatography, gel filtration, and HPLC) can be used. For example, a peptide substance is roughly extracted from an HL-60 cell homogenate and the resultant is fractionated. Then, a fraction showing the activity of stimulating an immune cell is obtained, thereby the peptide can be purified from the fraction. Further, the peptide of the present invention can also be produced by a genetic engineering technique.

The peptide of the present invention may bind to a receptor and exhibit the activity of stimulating an immune cell through G protein in the downstream of the receptor. Here, the phrase "the peptide binds to a receptor" means that the peptide can bind to a receptor of the peptide of the present invention with high affinity. The binding results in activation of the G protein, and subsequently, various physiological actions involved in the stimulation of the immune cell are caused. Note that the activation of the G protein can be evaluated by the methods described in the section (4) in Example 3 below. As the receptor of the peptide of the present invention, a protein having the amino acid sequence of SEQ ID NO: 52 is exemplified. The protein is registered as heat shock 70 kDa protein 8 isoform 1 with Entry No. HSP7C#HUMAN in Database: Swiss-PROT. The protein is present in a membrane. The peptide of the present invention may bind to the protein and exhibit the activity of stimulating an immune cell through a G protein in the downstream of the protein. The peptide of the present invention preferably bind to a protein having the amino acid sequence of SEQ ID NO: 52, that is, the peptide of the present invention preferably exhibits the activity of stimulating an immune cell by binding to the protein.

It has been found that the peptide of the present invention promotes the migration and the activation of a neutrophil (Example 3). Further, it has been found that, of the migration and activation of the neutrophil, the peptide of the present invention may promote only the migration in a certain case (for example, in the case of having a certain concentration), and promote only the activation of the neutrophil in another case (for example, in the case of having higher concentration than the former case) (Example 3). From the foregoing, it has been suggested that the peptide of the present invention diffuses from an inflammation site in an organism, thereby a neutrophil is induced (in this step, the neutrophil is not activated), and the peptide stops the migration of the neutrophil and activates the neutrophil in the vicinity of the inflammation site when the concentration of the peptide of the present invention is increased as the neutrophil approaches the inflammation site.

As described above, because the peptide of the present invention has the activity of stimulating an immune cell including a neutrophil, the peptide is useful for diagnosis, treatment, or prevention of a disease or state relating to the reduction in the number or hypofunction of the immune cell, or increase in the number or hyperfunction of the immune cell.

As the disease or state relating to the reduction in the number or hypofunction of the neutrophil, the neutropenia is exemplified.

In addition, the peptide is also useful for diagnosis, prevention, or treatment of a disease or state relating to the activation of an immune cell such as a neutrophil, which includes ischemia-reperfusion injury including ischemia-reperfusion injury derived from a myocardial infarction and an organ transplantation, I-type diabetes, and inflammatory diseases including rheumatism, acute nephritis, and fulminant hepatitis.

Further, the peptide of the present invention can be used in measurement of an activity of stimulating an immune cell, a method of screening an effective substance for clinical examination, treatment, and prevention of a disease or state relating to an immune cell such as a neutrophil, and a kit for clinical examination, treatment, and prevention of a disease or state relating to an immune cell such as a neutrophil.

Specifically, the peptide of the present invention or the antibody to the peptide or the like can be used in early detection, prevention, treatment, and the like of the above-mentioned neutropenia, ischemia-reperfusion injury, I-type diabetes, inflammatory diseases including rheumatism, acute nephritis, and fulminant hepatitis, and the like.

In addition, by using a substance suppressing the activity of the peptide of the present invention, such as the neutralizing antibody to the peptide of the present invention or the like, the infiltration of an immune cell such as a neutrophil is suppressed, thereby the peptide of the present invention can be also used in treatment of the above-mentioned ischemia-reperfusion injury, I-type diabetes, and inflammatory diseases including rheumatism, acute nephritis, fulminant hepatitis, and the like.

In addition, by administering the peptide of the present invention to stimulate a neutrophil, the peptide of the present invention can be used in treatment of the above-mentioned neutropenia and the like.

Further, by administering the peptide of the present invention in an excessive amount to prevent a neutrophil from transferring to an inflammation site, the above-mentioned ischemia-reperfusion injury, I-type diabetes, inflammation of inflammatory diseases including rheumatism, acute nephritis, fulminant hepatitis, and the like may be suppressed.

In the case where the peptide of the present invention is administered, two or more kinds of peptides chosen from the peptides (a) and (b) may be administered.

The antibody to the peptide of the present invention is useful for diagnosis and treatment of a disease or state relating to the activation of an immune cell such as a neutrophil. As the antibody, both a monoclonal antibody and a polyclonal antibody are useful and the monoclonal antibody is preferred. Note that, in the present invention, the monoclonal antibody includes a monoclonal antibody, a fragment of a monoclonal antibody, an F (ab')$_2$ fragment antibody, an F(ab') fragment antibody, scFv, Diabodies, and Minibodies. In producing the antibody, means well known to persons skilled in the art can be used. For example, for producing the monoclonal antibody, the peptide of the present invention is bound to a carrier protein and intraperitoneally injected with an adjuvant, as required, to thereby subject mammalians such as mice, rats, guinea pig, hamsters, and rabbits, and preferably mice, to an immune sensitization. The sensitization is repeated as required. When an appropriate antibody titer is obtained, an antibody-producing cell included in the spleen, the lymph node, the bone marrow, or the tonsil, and preferably in the spleen, is extracted, and the extracted cell and a myeloma cell, and preferably a myeloma cell which is the same kind as that of the mammalian, are fused. Then, by using a selection medium, a hybrid cell of the spleen cells, a hybrid cell of the myeloma cells, and an unfused cell are removed. The obtained hybridoma is subjected to a screening based on the reactibity with respect to the peptide of the present invention, thereby a cell producing a desired antibody to the peptide is obtained. From the obtained hybridoma, a desired antibody can be obtained by a mouse ascites method, or a culture method using an appropriate medium and incubator.

In the case where the peptide or antibody of the present invention is administered for treatment, the route of the administration is not particularly limited as long as the intended effect can be exhibited and the peptide or antibody can be administered safely. In addition, the formulation is not particularly limited as long as the intended effect can be exhibited and the peptide or antibody can be administered safely, and the formulation may be made according to the route of the administration or the like. For example, an injection is exemplified. Various pharmaceutically acceptable kinds of carriers such as an antiseptic agent, a humectant, an emulsifier, a dispersant, and a stabilizer can be added upon the formulation. The various kinds of the formulation can be produced by the step well known to persons skilled in the art. The dosage can be appropriately determined according to the purpose of the administration, the gender, body weight, and age of a patient, the formulation, the symptom, the route of the administration, the number of the administration, the course of the administration, and the like.

The antibody of the present invention can be evaluated from the aspect of the antigen-antibody reaction with the peptide of the present invention by the ELISA method well known to persons skilled in the art, and the like by using the peptide of the present invention as an antigen. In addition, the antibody of the present invention can be evaluated from an aspect of a suppression effect on the activity of stimulating a neutrophil by using the above-mentioned evaluation system relating to the stimulation of a neutrophil.

An diagnostic procedure of the present invention is a method of judging the onset or onset risk of the above-mentioned immune cell related diseases including the neutrophil, based on the amount of the peptide obtained by measuring the amount of the peptide chosen from the peptides (a) and (b). Here, the kind of the sample to be used is not particularly limited as long as the sample may contain the peptide of the present invention. The sample is preferably a body fluid such as blood, urine, and saliva, and particularly preferably the blood. The method of the measurement is preferably a method using an antibody to the peptide and particularly preferably the ELISA method. In the case of measuring the peptide of the present invention, two or more kinds of the peptides chosen from the peptides (a) and (b) may be measured.

In addition, the present invention also relates to a method of searching a peptide having an activity of stimulating an immune cell, which is characterized by including searching a sequence satisfying all of the requirements (I) to (V) and measuring the activity of the peptide having the sequence to stimulate an immune cell. In the case of searching the sequence satisfying all of the requirements (I) to (V), a program having means for inputting the sequences of candidate peptides, means for calculating about the requirements (I) to (V), and means for outputting the sequence satisfying the requirements (I) to (V) may be used.

EXAMPLES

Hereinafter, the present invention is explained in more detail by examples, but the present invention is not limited to these examples.

Example 1

Methods of Predicting and Identifying Activation Peptide (1) Method of Predicting Activation Peptide The amino acid sequence of the peptide activating a neutrophil was predicted and identified by a technique illustrated in FIG. 2. That is, at first, human mitochondrial protein data including the amino acid sequence were cyclopaedically collected from a protein data base, Swiss-Prot. Subsequently, of these data, peptide sequences which may be generated by a specific cleavage with mitochondrial processing peptidase or the like were compiled as a database. Then, of these peptide sequences complied as a database, selected was a predicted activation peptide which satisfies requirements about the chain length of the amino acid residue, the arrangement of the hydrophobic and hydrophilic residues, the charge of the whole molecule, the arrangement of the amino acid residues having charges, the arrangement of the amino acid residues having charges and aliphatic and aromatic side chains, and interrelation among their physicochemical characteristics, by using, as a model, a peptide, i.e. COSP-1, which had been identified as a neutrophil-activating peptide from an organism and confirmed to stimulate a neutrophil as a result of activation of a G protein.

That is, a sequence satisfying the following requirements 1) to 5) was used as a predicted activation peptide: 1) the chain length of the amino acid residues is 12 residues or more and to 36 residues or less; 2) when the sequence of the peptide is plotted as a known helical wheel (can be plotted with a commercially available Genetyx or the like), the sequence has a part of a amphipathic structure where an aliphatic or aromatic amino acid residue is located at one side and a hydrophilic amino acid residue is located at the opposite side; 3) the peptide has 3 or more positively charged amino acid residues (including an amino acid residue at the amino terminal) and the net charge of the peptide is +2 or more (provided that the carboxyl terminal is always charged negatively (−1)); 4) a positively charged amino acid residue is located at any one of 3rd or 4th residue, 7th or 8th residue, 10th or 11th residue, 14th or 15th residue, 18th residue, and 21st or 22nd residue, based on the positively charged amino acid residue (including a positive charge at the amino terminal); and 5) a side chain of any aromatic amino acid residue is not located between side chains of at least two positively charged amino acid residues on a side where hydrophilic amino acid residues are located (provided that the case where a Pro residue is present in a sequence among positively charged amino acids is excluded).

(2) Prediction Result

The inventors of the present invention have already isolated and purified neutrophil-activating peptides derived from mitochondria, i.e., fCytb and COSP-1, from an organism, and indicated that a large number of other neutrophil-activating peptides derived from a mitochondrial protein are present (Non-patent Documents 7 and 8, and Patent Document 1). If a large number of these unknown neutrophil-activating peptides are isolated and identified as conventionally done, much labor and time are required. Therefore, in the present invention, the sequences of the activation peptides were predicted by the above-mentioned method, and identification of the neutrophil-activating peptides was attempted by chemically synthesizing the activation peptides and verifying the activity of the predicted peptides.

In the prediction of the activation peptides, from the facts that COSP-1 activates a G protein directly and stimulates the migration and a β-hexosaminidase secretion of the neutrophil (Non-patent Documents 7 and 8) and the peptides activating the G protein have similarity in their secondary structures (Non-patent Documents 9 and 10), a peptide having a similar secondary structure as that of COSP-1 was defined as a predicted activation peptide (FIG. 2). As a result, 51 kinds of different peptide sequences shown in Table 1 were obtained, and almost all the sequences were peptides derived from mitochondrial proteins coded in the nuclear genes. Note that the peptide of SEQ ID NO: 41 is a negative control peptide having a net charge of −3. In addition, the peptide of SEQ ID NO: 17 has a sequence including a cleavage point for chymotripsin, and the other peptides each have a sequence including a cleavage point for a mitochondrial processing enzyme. In addition, because the peptides of SEQ ID NOS: 21 and 30 each have a sequence including a Pro residue among positively charged amino acids, the peptides do not satisfy the requirement (5) a side chain of any aromatic amino acid residue is not located between side chains of at least two positively charged amino acid residues on a side where hydrophilic amino acid residues are located, but other peptides satisfy the above-mentioned requirement (5).

Example 2

Peptide Synthesis

All of the peptides which have been predicted to have activities, shown in Table 1, and the peptides used in receptor identification experiments were chemically synthesized by a solid phase method using the Fmoc method (Non-patent Document 11). The synthesis was performed using a multi-peptide synthesis apparatus (manufactured by Advanced ChemTech) or a hand-control stirring apparatus for peptide synthesis (manufactured by HiPep Laboratories). As a protecting group with respect to the side chain of each amino acid, a t-butyl ester (OBut) group was used for Asp and Glu, a t-butyl (But) group was used for the side chain of Ser, Thr, and Tyr, a t-butyloxycarbonyl (Boc) group was used for Lys and Trp, a 2,2,4,6,7-pentamethyldihydrobenzofuran-5-sulfonyl (Pbf) group was used for Arg, and a triphenylmethyl (Trt) group was used for His, Asn, Gln, and Cys.

(1) Extension and Deprotection of Peptide Chain and Desorption from Resin

The peptide chain was extended by repeating cleavage of an Fmoc group with 25% piperidine and condensation of an Fmoc amino acid by the DIC-HOBt method, HBTU-DIEA method, or HATU-DIEA method (Non-patent Document 11). That is, the resin in which the Fmoc amino acid corresponding to the amino acid residue at the C-terminal was introduced was washed with NMP and DMF and swelled in the NMP for 30 minutes, and then, the Fmoc group as a protecting group of the N-terminal was cleaved by a treatment using 25% piperidine. Next, 2.5 equivalents of each Fmoc amino acid corresponding to the second amino acid from the C-terminal, DIC, and HOBt were added thereto, and the mixture was reacted in the NMP for 2 hours to be condensed. In the manual synthesis, the completion of the reaction was confirmed by a ninhydrin test (Non-patent Document 11). In the case of insufficient reaction, 2.25 equivalents of HBTU, 2.5 equivalents of HOBt, and 4.5 equivalents of DIEA were added, followed by a condensation reaction again for 2 hours. Further, in the case of insufficient reaction after repeated condensation reactions, 9 equivalents of DIEA, 5 equivalents of HOBt, and 4.5 equivalents of HBTU with respect to the amount of the resin were added, or the reaction time was prolonged to 4 hours or 6 hours to proceed the condensation reaction. Thus, the cleavage of the Fmoc group with piperidine and the condensation reaction of the Fmoc amino acid were repeated, thereby the peptide chain was extended.

Deprotection of the synthesized peptide and desorption from the resin were performed by a treatment using Reagent K (TFA:phenol:dimethyl sulfide:water:ethanediol=82.5:5:5:5:2.5) for 3 hours. After the completion of the reaction, the resultant was washed with diethyl ether five times and the obtained synthesized product was dissolved with 0.1% TFA-$H_2O$. The resultant was transferred in a 15-ml conical tube and centrifuged (5,000 rpm, 10 minutes, 4° C). Then, the supernatant was collected and lyophilized, thereby a crude peptide was obtained.

(2) Analysis and Purification of Synthesized Peptide

The crude peptide was analyzed by reverse-phase high performance liquid chromatography (RP-HPLC). In the analysis, a Develosil ODS-HG column (4.6×150 mm) was used, and the elution was performed in the presence of 0.1% TFA by a concentration gradient of acetonitrile at a flow rate of 1 ml/min. Each peak fraction was collected by measurement of absorption at 214 nm. The mass of the peptide contained in the obtained peak fraction was measured by matrix assisted laser desorption ionization time of flight mass spectrometer (MALDI-TOF-MS) apparatus (manufactured by Applied Biosystems). That is, the eluted fraction and a saturated solution of α-cyano-4-hydroxycinnamic acid (α-CHCA) as a matrix for the measurement were mixed at a ratio of 1:1, and 1 μl of the mixture was put on a sample plate and dried. Next, the sample plate was irradiated with laser with the MALDI-TOF-MS apparatus and the molecular weight was measured, thereby the intended peptide was identified.

The intended peptide which had been identified with the mass analysis was purified using a Develosil ODS-HG column (250×250 mm) by eluting in a concentration gradient of acetonitrile in the presence of 0.1% TFA at a flow rate of 5 ml/min, and collecting an intended peak fraction as a result of detection of absorption at 214 nm. After that, the obtained peptide solution was lyophilized and the purity thereof was tested using HPLC. The peptide whose purity was confirmed was subjected to a mass analysis by MALDI-TOF-MS again, thereby the molecular weight was confirmed to be right. After the acid hydrolysis, the peptide was confirmed to be the intended product by an amino acid composition analysis. That is, the purified peptide was treated in the presence of 1% phenol in a gas phase of 6 N—HCl at 110° C. for 22 hours to hydrolyze the peptide. After the hydrolysis, the sample was dried under reduced pressure, and dissolved in 0.01 N—HCl (1 to 2 nmol/10 μl). Then, the sample was analyzed with an amino acid composition analyzer (manufactured by Hitachi, Ltd.) After that, the number of the collected moles of the amino acid was calculated based on glycine, alanine, and the like, which were stable to the acid hydrolysis. The sample was dispensed based on the quantitative value and stored at −80° C.

Example 3

Identification of Functional Peptide (1) Culture of Cell and Differentiation Into Neutrophil-like Cell HL-60 cells were cultured in a 75-$cm^2$ culture flask (Non-treated Flask manufactured by Iwaki Glass Co., Ltd.) by using a medium, which was obtained by adding a fetal bovine serum (FBS) inactivated by heat to a RPMI-1640 medium so as to have a final concentration of 10% (10% FBS-RPMI1640 medium), and being left at stand in the presence of 5% $CO_2$ in an incubator. In this time, the cells were subcultured at a cell density of $1.0 \times 10^5$ cells/ml to $1.5 \times 10^6$ cells/ml, the number of cells was counted using a microscope, and the state of the cells was also confirmed.

The HL-60 cells were differentiated into neutrophil-like cells by setting the cell density in the flask to about $1.0 \times 10^6$ cells/ml, adding dibutylyl-cAMP (db-cAMP) as a differentiation-inducing agent so as to have a final concentration of 500 μM, and incubating the cells in the presence of $CO_2$ at 37° C. for 3 days.

(2) Stimulation of Cell and Measurement of β-Hexosaminidase-secreting Activity

The cells were collected by centrifuging the suspension of the differentiated HL-60 cells (1,000 rpm, 5 minutes, 4° C.). After that, the following operation was repeated three times to wash the cells: Hepes buffered Hank's solution (HBHS) containing ice-cooled 0.1% BSA (1.2 mM $CaCl_2.2H_2O$, 5.4 mM KCl, 0.44 mM $KH_2PO_4$, 0.49 mM $MgCl_2.6H_2O$, 0.41 mM $MgSO_4.7H_2O$, 136.9 mM NaCl, 0.34 mM $Na_2HPO_4$, 10 mM Hepes, 4.2 mM $NaHCO_3$, 5.5 mM D-glucose, pH 7.4) was added to the cells; the mixture was suspended by inversion; and the mixture was centrifuged again (1,000 rpm, 5 minutes, 4° C.). Subsequently, HBHS was added so that the mixture has a cell density of $5.6 \times 10^6$ cells/ml and suspended. Then, DNase I and cytochalasin B were each added so as to have a final concentration of 5 μg/ml, and the cell suspension was dispensed in an amount of 90 μl ($5 \times 10^5$ cells) on ice. The cells were stimulated with the peptide by the following procedure: at first, the tubes containing dispensed cell suspension were preincubated at 37° C. for 10 minutes; 10 μl of the peptide solution prepared to have higher concentration than the final concentration by 10 times were added to each tube; and the reaction was performed at 37° C. for 10 minutes. In addition, in the case of a measurement of β-hexosaminidase-secreting activity by a mixture containing 10 kinds of peptides, each peptide solution prepared to have higher concentration than the final concentration by 100 times was mixed in an equal amount and the cells were stimulated with 10 μl of the obtained mixed peptide solution. After the cell stimulation for 10 minutes, 100 μl of an ice-cooled stop solution (25 mM Tris, 123 mM NaCl, 2.7 mM KCl, pH 7.4) were added, and immediately, the mixture was centrifuged (5,000 rpm, 1 minute, 4° C.). 200 μl of the obtained supernatant were transferred to a new tube.

The amount of β-hexosaminidase released in the supernatant of the reaction solution was measured by an enzyme reaction using p-nitrophenyl-N-acetyl-μ-D-glucosaminide as a substrate (Non-patent Document 12). That is, the supernatant of the reaction solution was dispensed in an amount of 90 μl to a 96-well plate. 60 μl of a substrate solution (10 mM p-nitrophenyl-N-acetyl-μ-D-glucosaminide, 40 mM citrate, 70 mM $Na_2HPO_4$, pH 4.5) were added to each well, followed by incubation at 37° C. for 1 hour. After the reaction, 100 μl of a stop solution (0.4 M glycine, pH 10.7) were added to each well and a color of the released p-nitrophenol was developed. The color development was measured with a plate reader at adsorption at 405 nm (reference: 492 nm). The all amount of β-hexosaminidase contained in the cells was quantified by treating the cells with Triton X-100 having a final concentration of 0.05%. In addition, the amount of β-hexosaminidase secreted by stimulation of 10 μM fMLP was also measured, and the ratio of the secretion amount by stimulation with each peptide to the above sectretion amount by stimulation with fMLP.

(3) Measurement of Migration Activity

The cells were collected by centrifuging the suspension of the differentiated HL-60 cells (1,000 rpm, 5 minutes, 4° C.). After that, the following operation was repeated three times to wash the cells: 10% FBS-RPMI1640 was added to the cells; the mixture was suspended by inversion; and the mixture was centrifuged again (1,000 rpm, 5 minutes, 4° C.). Then, a medium (10% FBS-RPMI1640) was added so that a cell density was $4 \times 10^6$ cells/ml, thereby a cell suspension was prepared. Subsequently, 1 ml of each peptide solution (dissolved in 10% FBS-RPMI 1640) was transferred to each well of a 24-well plate, and the plate was incubated at 37° C. for 20 minutes. After that, 500 μl of the cell suspension ($2 \times 10^6$ cells) were put in Chemotaxicell (KURABO INDUSTRIES LTD., 3 μm) and the Chemotaxicell was set in a plate, followed by incubation in the presence of 5% $CO_2$ at 37° C. for 1 hour. Then, the Chemotaxicell was removed and the solution in each well of the plate was pipetted. The cells migrated to the plate side was suspended well and the number of the cells were measured. Note that the migration activity by the peptide was represented by a ratio of the number of the cells to the number of the cells passing the Chemotaxicell at the time of non-stimulation (Chemotaxis Index, CI).

(4) Measurement of G Protein Activation Ability

The cells were collected by centrifuging the suspension of the differentiated HL-60 cells (1,000 rpm, 5 minutes, 4° C.). After that, the following operation was repeated three times to wash the cells: ice-cooled PBS was added to the cells; the mixture was suspended by inversion; and the mixture was centrifuged (1,000 rpm, 5 minutes, 4° C.). Then, the precipitated cells were suspended in a buffer for preparing a cell membrane fraction (20 mM Tris-HCl, 250 mM sucrose, 1.5 mM $MgCl_2$, 3 mM benzamidine hydrochloride monohydrate, 1 μM leupeptin, 1 μM PMSF, 2 μg/ml trypsin inhibitor, pH 7.5) and a cell homogenate was prepared using nitrogen pressing-depressing type cell homogenizing apparatus (nitrogen pressure: 350 psi). After that, the resultant was ultracentrifuged (20,000 g, 4° C., 30 minutes) to remove the supernatant, and the precipitate was suspended in a membrane fraction buffer (20 mM Tris-HCl, 1 mM EDTA, 1 mM DTT, 77.5 mTIU/ml aprotinin, pH 7.5) and used as a cell membrane fraction. After dispensed, the cell membrane fraction was stored at -80° C. The activity of the G protein was quantified using the activity to hydrolyze GTP to GDP as an index. That is, after 5 μl of the peptide aqueous solution were put in a reaction tube under ice cooling, 20 μl of a buffer for measuring a G protein activity (Hepes 50 mM, 1 mM EDTA, 1 mM DTT, 10 nM [γ-$^{32}$P]GTP, 50 nM GDP, 1.1 mM $MgSO_4$, 0.1 mg/ml BSA, pH 8.0) were added to the tube. Next, 5 μl of the cell membrane fraction of the differentiated HL-60 cells (25 ng protein/5 μl) or bovine $G_{i1}$-G protein (6 pmol/5 μl) which had been expressed using *E. coli* and purified were added to each reaction tube to start a reaction. After incubation at 30° C. for 10 minutes, an ice-cooled reaction stop solution (5% charcoal, 50 mM $NaHPO_4$) was added thereto. The mixture was centrifuged (15,000 rpm, 1 minute, 4° C.), and the radioactivity of the supernatant was measured.

(5) Identification of Functional Peptide by Evaluating the Activity

In order to clarify whether the peptide suggested to have the activity has the activity actually or not, the HL-60 cells differentiated into the neutrophil-like cells were stimulated to examine whether the cells showed the β-hexosaminidase-secreting activity or not. As a result, it was revealed that 44 sequences of predicted 51 sequences had the activity and 25 sequences of these sequences functioned at a concentration of 10-6 M or less (Table 1). Therefore, these peptides having the neutrophil-activating ability were genetically named as mitocryptide. Next, the migration activity of 44 kinds of the peptides having the β-hexosaminidase-secreting activity was also measured, and its concentration dependency was compared with that of β-hexosaminidase-secreting activity. As a result, it was indicated that all 44 kinds of peptides had the migration activity (FIGS. 3 to 8 show the concentration dependency in the stimulation of the β-hexosaminidase secretion and the migration by these peptides). That is, mitocryptide-3, -4, -5, -14, -15, and -16 exhibited significant β-hexosaminidase-secreting activity even at a concentration of 100 nM or less ($EC_{50}$'s: mitocryptide-3, 200 nM; mitocryptide-4, 300 nM; mitocryptide-5, 380 nM; mitocryptide-14, 110 nM; mitocryptide-15, 100 nM; and mitocryptide-16, 120 nM) (FIGS. 3 and 6). It was revealed that all mitocryptide-3-2, -5-2, and -10-2 obtained by extending the C-terminal of mitocryptide-3, -5, and 10, respectively, had higher activity compared to the peptides before the extension ($EC_{50}$'s: mitocryptide-3-2, 150 nM; mitocryptide-5-2, 200 nM; mitocryptide-10, 8 μM; and mitocryptide-10-2, 6 μM) (FIGS. 3 to 5). Of these peptides, the migration activity of mitocryptide-3 and -3-2 were confirmed at the concentration lower than the concentration at which β-hexosaminidase-secreting activity was confirmed. On the contrary, the migration activity and the β-hexosaminidase-secreting activity of mitocryptide-4, -5, -5-2, -14, and -15 were confirmed at the almost same concentration (FIGS. 3 and 6). Thus, it was revealed that the activation peptides identified in the research of the present invention were classified into the peptides in which the migration activity was confirmed at the lower concentration than the β-hexosaminidase-secreting activity and the peptides in which the migration activity and the β-hexosaminidase-secreting activity were confirmed at the almost same concentration (FIGS. 3 to 7). In addition, the migration activity of these peptides was subjected to desensitization with increasing concentration of the peptides. It was revealed that particularly the migration activity of the mitocryptide-3, -4, -5, and -14 was subjected to desensitization completely (FIGS. 3 to 7).

Thus, it was revealed that the activation peptides identified in the present invention had not only the β-hexosaminidase-secreting activity but also the migration activity, in the concentration dependency, the peptides were classified into the peptides in which the migration activity was confirmed at the lower concentration than the β-hexosaminidase-secreting activity and the peptides in which the migration activity and the β-hexosaminidase-secreting activity were confirmed at the almost same concentration, and that the migration activity of all activation peptides was subjected to desensitization with increasing concentration of the peptides (FIGS. 3 to 8). These results indicate that the neutrophil may recognize the concentrations of the identified activation peptides strictly, and is migrated and activated. Further, there were probably the following different function mechanisms in the neutrophil: in the case of recognition of the peptide which exhibited the migration activity at lower concentration than the concentration which exhibited β-hexosaminidase-secreting activity, such as mitocryptide-3, the neutrophil was not activated during the migration, activated for the first time when the neutrophil reach an inflammation site; and on the contrary, in the case of the peptide exhibiting the β-hexosaminidase-secreting activity and the migration activity at the almost same concentration, such as mitocryptide-5, the neutrophil was activated at the same time of the migration.

Because the identified peptides are suggested to be peptides activating the neutrophil as a result of the activation of a G protein, their receptors may conjugate the G protein. It is reported that the G protein is activated by amphipathic peptides and these peptides have a common point in the secondary structure (Non-patent Documents 9 and 10). Then, whether the identified peptides activate the G protein or not was examined (FIG. 9). As a result, it was revealed that the peptides exhibiting high stimulation activity with respect to neutrophil-like differentiated HL-60 cells, such as mitocryptide-3 and-5, activated the Gprotein in the differentiated HL-60 cell membrane fraction and these peptides also activated the purified $G_{i1}$ protein. Therefore, at least one receptor of the activation peptides was suggested to be a receptor conjugating the G protein. Note that, in FIG. 9, fMLP and mas7 each refer to synthesized peptides activating the G protein and are each used as a positive control.

As shown in Table 1, the identified activation peptides have little homology in the amino acid sequence thereof, but if they bind to the same receptor conjugating the G protein from the identity in the secondary structure, a concerted effect may be caused in the case of stimulating the G protein by multiple peptides simultaneously. Then, 10 kinds of the peptides having lower concentrations than the case of stimulating the β-hexosaminidase secretion were mixed, and whether the mixture stimulate the HL-60 cell differentiated into the neutrophil-like cell and induces the β-hexosaminidase secretion or not was examined. That is, the mitocryptide-3, -4, -5, -6, -7, -8, -9, -10, -11, and 12 exhibiting the concentration dependency and having high activity shown in FIG. 10-A were mixed at each concentration not stimulating the β-hexosaminidase secretion alone (mitocryptide-3, 50 nM; mitocryptide-4, 50 nM; mitocryptide-5, 10 nM; mitocryptide-6, 30 nM; mitocryptide-7, 50 nM; mitocryptide-8, 50 nM; mitocryptide-9, 100 nM; mitocryptide-10, 100 nM; mitocryptide-11, 200 nM; and mitocryptide-12, 100 nM), and the β-hexosaminidase-secretion-simulating activity by the stimulation with the mixed peptide was examined. As a result, the mixture of 10 kinds of peptides exhibited 53.7% of the secretion activity with respect to the β-hexosaminidase secretion by the stimulation with 10 μM fMLP (FIG. 10-B). Thus, it was indicated that the peptides function concertedly, and stimulate the differentiated HL-60 cell (FIG. 10).

It has been conventionally considered that, in the case of endogenous functional peptides having different primary sequences, each peptide has a specific receptor and fulfill the function by acting to the receptor (a to d of FIG. 11(A) and additive signaling in FIG. 11(B)). Therefore, even if peptides each having a concentration not causing the cell activation a remixed, no activation must be confirmed. However, the activation was confirmed by mixing multiple peptides each having the concentration at which a single peptide does not cause the cell activation at all, and hence, it can be conceived that there is a new receptor recognizing multiple peptides as if they are one ligand and the receptor causes response of the neutrophil (e to m of FIG. 11(A) and accumulative signaling in FIG. 11(B)). The inventors of the present invention named said signal transduction system as "accumulative signaling" (FIG. 11). As described above, because the identified activation peptides do not have homology in the primary structure but have homology in the secondary structure, the new receptor may recognize the secondary structure but not the primary structure.

TABLE 1

Sequences of peptides predicted as peptides activating
the neutrophil and their β-hexosaminidase-secreting activity

| No. | Name | Sequence | MW | EC$_{50}$ (μM) | n | Activity |
|---|---|---|---|---|---|---|
| 001 | | MASRLLRGAGTLAAQALRARGPSGAAAMRSM | 3100.67 | 23.0 | 6 | ● |
| 002 | | MASRLLRGAGTLAAQALRARGPSGAAAMR | 2882.40 | | 4 | ▲ |
| 003 | | MASRLLRGAGTLAAQALRAR | 2083.49 | | 4 | ▲ |
| 004 | | MASRLLRGAGTLAAQALRA | 1927.30 | 15.0 | 4 | ● |
| 005 | | MASRLLRGAGTLAAQALR | 1856.22 | | 4 | ▲ |
| 006 | | MGGLWRPGWRCVPFCGWRWI | 2463.97 | | | ▲ x |
| 007 | mitocryptide-10 | MSVLTPLLLRGLTGSARRLPVPRAK | 2703.33 | 8.0 | 7 | ○ |
| 008 | | MLGQSIRRFTTSVVR | 1751.08 | 100.0< | | ▲ |
| 009 | mitocryptide-12 | MAVVGVSSVSRLLGRSRPQLGRPM | 2554.07 | 5.0 | 6 | ○ |
| 010 | | MLGQSIRRFTTSVVRR | 1907.27 | 40< | 7 | ● |
| 011 | mitocryptide-7 | MQALRVSQALIRSFSSTARNR | 2392.76 | 1.7 | 7 | ◉ |
| 012 | mitocryptide-22 | MLRNLLALRQIGQRTISTASRRH | 2692.18 | 0.78 | 6 | ○ |
| 013 | | MALPLRPLTRGL | 1337.69 | 30< | 7 | ● |
| 014 | | MALPLRPLTRGLASAAKGGHGGA | 2202.61 | 18.0 | 7 | ● |
| 015 | mitocryptide-5 | MFPLVKSALNRLQVRSIQQTMARQ | 2816.38 | 0.38 | 6 | ◉ |
| 016 | | MPLLRGRCPARRHYRRLALLGLQPAPRFA | 3387.13 | 20< | 6 | ● |
| 017 | | FTTFLTPAAYVLGNLKQFRRN | 2457.86 | 40< | 1 | ▲ |
| 018 | mitocryptide-9 | MLATRVFSLVGKRAISTSVCVR | 2394.92 | 6.1 | 6 | ○ |
| 019 | mitocryptide-3 | MLWNLLALHQIGQRTISTASHRH | 2684.12 | 0.23 | 8 | ◉ |
| 020 | | MRGAGPSPRQSPRTLRPDPGPAMSFFRR | 3126.61 | no. activity | 4 | x |
| 021 | | MAIQFRSLFPLALPGMLALLGWWWFFSRK | 3484.27 | | 4 | ● |
| 022 | mitocryptide-19 | MAAAALGQIWARKLLSVPWLLCGPRRY | 3041.71 | 0.8 | 6 | ◉ |
| 023 | mitocryptide-4 | MAALLLRHVGRHCLRAHFSPQLCIRNAVPL | 3394.13 | 0.3 | 7 | ◉ |
| 024 | mitocryptide-6 | MLRLPTVFRQMRPVSRVLAPHLTRAY | 3109.79 | 1.1 | 6 | ◉ |
| 025 | mitocryptide-8 | MALVHKLLRGTYFLRKFSKPTSAL | 2778.40 | 1.9 | 6 | ◉ |
| 026 | | MAAVVALSLRRRLPATTLGGACLQASRG | 2840.40 | 10.0 | 6 | ● |
| 027 | | MQRAVSVVARLGFRLQAFPPALCRPLSC | 3087.76 | 30< | 7 | ● |
| 028 | mitocryptide-11 | MAAQCVRLARRSLPALALSLRPSPRLL | 2960.64 | 3.5 | 6 | ○ |
| 029 | | MAAPRAGRGAGWSLRAWRALGGIRWGRRPRL | 3460.08 | 50< | 12 | ● |
| 030 | mitocryptide-17 | MLIPFSMKNCFQLLCNCQVPAAGFK | 2804.46 | 1.0 | 6 | ○ |
| 031 | mitocryptide-5-2 | MFPLVKSALNRLQVRSIQQTMARQSHQKRT | 3554.20 | 0.2 | 6 | ◉ |
| 032 | mitocryptide-3-2 | MLWNLLALHQIGQRTISTASHRHFKNKVPEKQK | 3911.59 | 0.15 | 6 | ◉ |

TABLE 1-continued

Sequences of peptides predicted as peptides activating the neutrophil and their β-hexosaminidase-secreting activity

| No. | Name | Sequence | MW | EC$_{50}$ (µM) | n | Activity |
|---|---|---|---|---|---|---|
| 033 | mitocryptide-10-2 | MSVLTPLLLRGLTGSARRLPVPRAKIHS LPPEGK | 3662.44 | 6.0 | 6 | ○ |
| 034 | mitocryptide-13 | MAALKALVSGCGRLLRGLLAGPAATSWS RLPARG | 3422.12 | 0.15 | 6 | ◎ |
| 035 | mitocryptide-20 | MSVVRSSVHARWIVGKVIGT | 2182.62 | 3.0 | 6 | ○ |
| 036 | | MLRALSRLGAGTPCRPRAPLVLPARGRK TRH | 3409.13 | 20.0 | 6 | ● |
| 037 | mitocryptide-14 | MFRRPVLQVLRQFVRH | 2082.55 | 0.11 | 7 | ◎ |
| 038 | | MPAPRAPRALAAA | 1292.57 | no. activity | 4 | x |
| 039 | | MAASVVCRAATAGAQVLLRARRSPALLR TPALRS | 3535.24 | 40< | 7 | ● |
| 040 | mitocryptide-18 | MKLLTRAGSFSRFY | 1677.00 | 2.0 | 7 | ◎ |
| 041 | | MGLEDEQKMLTES | 1510.69 | no. activity | 5 | x |
| 042 | mitocryptide-23 | MEGLAVRLLRGSRLLRRNFLTCLSSWKI PPHVS | 3807.58 | 15< | 3 | ○ |
| 043 | mitocryptide-21 | MFSRAGVAGLSAWTLQPQWIQVRNM | 2848.34 | 1.3 | 6 | ○ |
| 044 | | MAAPAVSGLSRQVRCFSTSVVRPF | 2567.03 | 30< | 5 | ● |
| 045 | | MAAALLARASGPARRALCPRAWRQ | 2594.11 | 30< | 6 | ● |
| 046 | mitocryptide-24 | MLPAALLRRPGLGRLVRHARAY | 2488.05 | 5< | 5 | ○ |
| 047 | | MLSALARPVSAALRRSFSTSAQNN | 2548.91 | 20< | 6 | ● |
| 048 | mitocryptide-15 | MFPLARNALSSLKIQSILQSMARH | 2713.26 | 0.1 | 6 | ◎ |
| 049 | | MALRAKAEVCMAVPWLSLQRAQAL | 2657.25 | 2.0 | 5 | ● |
| 050 | | MALLTAAARLLGTKNASCLVLAARHAS | 2724.28 | 7.0 | 6 | ● |
| 051 | mitocryptide-16 | MAAGFGRCCRVLRSISRFHWRSQHT | 2963.45 | 0.3 | 4 | ◎ |

Note that in tables, ◎ represents a peptide in which the β-hexosaminidase-secreting activity was confirmed at a concentration of 300 nM or less, ○ represents a peptide in which the β-hexosaminidase-secreting activity was confirmed at a concentration of 1 µM or less, ● represents a peptide in which the β-hexosaminidase-secreting activity was confirmed at a concentration of 10 µM or less, ▲ represents a peptide in which the β-hexosaminidase-secreting activity was confirmed at a concentration of 100 µM or less, and x represents a peptide in which no β-hexosaminidase-secreting activity was confirmed. In addition, the activity of the peptide in which multiple symbols are shown indicate that the results belonging to multiple categories were obtained in the performed experiments.

Example 4

Identification of Functional Peptide-receptor and Intracellular Signal Transduction Pathway From the experiment described in Example 3, the functional peptides activating the neutrophil was identified. Next, the receptors of the functional peptides were identified using a chemical cross-linking method.

At first, regarding to the mitocryptide-3 and -5, which showed the highest activities of these identified functional peptides, peptides in which Cys residues were added to the their N-terminal ([Cys$^0$]mitocryptide-3 and [Cys$^0$]mitocryptide-5), a peptide in which a Cys residue was added to the C terminal of the mitocryptide-3 ([Cys$^{24}$]mitocryptide-3), and peptides in which biotin was introduced into the N terminals of these peptides and the mitocryptide-3 and -5 (N-biotinyl-mitocryptide-3, N-biotinyl-mitocryptide-5, N-biotinyl-[Cys$^0$]mitocryptide-3, N-biotinyl-[Cys$^0$]mitocryptide-5, and N-biotinyl-[Cys$^{24}$]mitocryptide-3) were chemically synthesized as described in Example 2.

In order to confirm that the synthesized functional peptide derivatives have activities, the neutrophil-like differentiated HL-60 cells were stimulated with the functional peptide derivatives (final concentration 10 µM) based on the method described in Example 3-(2). As shown in FIG. 12, the following were revealed: all of the derivatives stimulated the cells and promoted the β-hexosaminidase-secretion; and a Gi protein is involved in their intracellular signal transduction because the stimulation was inhibited when the cells pretreated with pertussis toxin (PTX) having a final concentration of 50 ng/ml for 16 hours, which inhibited the Gi protein specifically, was used.

Thus, it was confirmed that the synthesized functional peptide derivatives had the activities. Therefore, subsequently, in order to identify the binding sites of the functional peptides in the cells, these peptides (final concentration 10 μM) were incubated with the neutrophil-like differentiated HL-60 cells or undifferentiated HL-60 cells prepared in Example 3-(3) at 37° C. for 30 minutes. After that, the obtained cell suspension was centrifuged (1,000 rpm, 5 minutes, 4° C.) and the supernatant was removed. Further, HBHS was added and the mixture was centrifuged to wash the cells. Then, the cells were resuspended in HBHS. A streptavidin-HBHS labeled with a fluorescence, Alexa488 (Molecular probe, Invitrogen Corporation.) was added thereto, and the mixture was centrifuged, and the supernatant was removed. Further, the following operation was repeated three times to wash the cells: HBHS was added and the mixture was centrifuged. Then, the resultant cells were observed with a fluorescence microscope. As a result, as shown in FIG. 13, it was revealed that the binding sites of these functional peptides were present in the cell membranes by the following results: N-biotinyl-[Cys$^0$]mitocryptide-3 was bound to the surfaces of the neutrophil-like differentiated HL-60 cells specifically but less bound to the surfaces of the undifferentiated HL-60 cells (FIG. 13-A); no binding was confirmed at all in the peptide which did not activate the neutrophil and served as a control (N-biotinyl-Cys-Gln-Leu-Trp-Ala-Val-Gly-Ser-Phe-Met-NH$_2$) (FIG. 13-B); and N-biotinyl-[Cys$^0$]mitocryptide-5 was bound to the surfaces of the cells specifically as N-biotinyl-[Cys$^0$]mitocryptide-3.

Then, in order to identify directly the receptor molecules to which these functional peptides are bound, the following chemical crosslinking experiment was performed. That is, the HL-60 cells differentiated into the neutrophil-like cells were suspended in HBHS (not containing 0.1% BSA). The suspension was centrifuged (1,000 rpm, 5 minutes, 4° C.) and the supernatant was removed. The cells were suspended again in the HBHS not containing BSA so as to have the cell density of 5.6×10$^6$ cells/ml. The obtained cell suspension was preincubated at 37° C. for 10 minutes at first, and ¹/₁₀ volume of mitocryptide-3 and -5, [Cys$^0$]mitocryptide-3, [Cys$^0$]mitocryptide-5, [Cys$^{24}$]mitocryptide-3, and peptides obtained by introducing biotin into the N terminals thereof (N-biotinyl-mitocryptide-3, N-biotinyl-mitocryptide-5, N-biotinyl-[Cys$^0$]mitocryptide-3, N-biotinyl-[Cys$^0$]mitocryptide-5, and N-biotinyl-[Cys$^{24}$]mitocryptide-3) were added to have the final concentration of 10 μM, followed by incubation at 37° C. for 30 minutes. After that, the cell suspension was centrifuged (5,000 rpm, 4° C., 1 minute) and the supernatant was removed. The resultant cells were resuspended in HBHS not containing BSA and centrifuged again to wash the cells. 1 ml of a buffer for dissolving cells (100 mM NaCl, 20 mM Tris-HCl, 1 mM EDTA, 77.5 mTIU/ml aprotinin, 1 μM leupeptin, 1 μg/ml pepstatin A, 1 μg/ml phosphoramidone, 1% CHAPS, pH 7.5) with respect to 1 ml of the original cell suspension was added to the cell precipitate, and the mixture was incubated at 4° C. for 30 minutes to dissolve the cells, thereby a cell lysate was prepared. The cell lysate was centrifuged (15,000 rpm, 4° C., 15 minutes) and the supernatant was centrifuged again in the same condition. The obtained supernatant was incubated with streptavidin beads at 4° C. for 30 minutes, then, the beads were washed by centrifugation with the buffer for dissolving cells three times. Further, the beads were treated by heat at 100° C. for 10 minutes in the buffer for dissolving cells, and the mixture was centrifuged. The obtained supernatant was subjected to an SDS gel electrophoresis to separate the contained protein. Then, the gel was stained by silver stain method, thereby the proteins were analyzed. As a result, as shown in FIG. 14, five bands indicating specific binding to N-biotinyl-[Cys$^0$]mitocryptide-3 and N-biotinyl-[Cys$^{24}$]mitocryptide-3 were detected. Further, the sample was analyzed by second-dimensional electrophoresis shown in FIG. 15. As a result, two specific spots were detected (FIG. 15-A). Therefore, the protein was extracted and degraded with trypsin, and then, the degraded proteins were analyzed by mass spectrometry. As a result, one of these proteins (corresponding to band b in FIG. 14) was suggested to be heat shock 70 kDa protein 8 isoform 1 (SEQ ID NO: 52). Further, the protein was subjected to western blotting analysis with a commercially available antibody to the protein (Affinity BioReagents, Inc., MA3-007), as a result, the protein was recognized by the antibody to heat shock 70 kDa protein as shown in FIG. 15-B. Further, it was revealed that the protein was also bound to N-biotinyl-[Cys$^0$]mitocryptide-5 and, in the binding, the protein was competitive with other identified functional peptides including mitocryptide-3, and hence, it was suggested that the protein is a receptor common to the functional peptides identified in the present invention or one of the common receptors.

INDUSTRIAL APPLICABILITY

The peptide and the antibody to the peptide of the present invention can be suitably used in diagnosis, prevention, treatment, and the like of an immune cell related disease, and particularly a neutrophil.

The invention claimed is:

1. An isolated peptide selected from group (a) or (b):
   (a) a peptide consisting of the amino acid sequence of SEQ ID NO: 15, 19, 23, 37, 48, or 51; and
   (b) a peptide consisting of the amino acid sequence of SEQ ID NO: 15, 19, 23, 37, 48, or 51 in which one or two amino acids are deleted, substituted, inserted, or added, and having an activity of stimulating a neutrophil.

2. The isolated peptide according to claim 1, wherein a receptor of the peptide is a protein containing the amino acid sequence of SEQ ID NO: 52.

* * * * *

SEQUENCE LISTING

```
<160> NUMBER OF SEQ ID NOS: 52

<210> SEQ ID NO 1
<211> LENGTH: 31
<212> TYPE: PRT
<213> ORGANISM: Homo sapiens

<400> SEQUENCE: 1

Met Ala Ser Arg Leu Leu Arg Gly Ala Gly Thr Leu Ala Ala Gln Ala
1               5                   10                  15

Leu Arg Ala Arg Gly Pro Ser Gly Ala Ala Ala Met Arg Ser Met
            20                  25                  30
```

<210> SEQ ID NO 2
<211> LENGTH: 29
<212> TYPE: PRT
<213> ORGANISM: Homo sapiens

<400> SEQUENCE: 2

Met Ala Ser Arg Leu Leu Arg Gly Ala Gly Thr Leu Ala Ala Gln Ala
1               5                   10                  15

Leu Arg Ala Arg Gly Pro Ser Gly Ala Ala Ala Met Arg
            20                  25

<210> SEQ ID NO 3
<211> LENGTH: 20
<212> TYPE: PRT
<213> ORGANISM: Homo sapiens

<400> SEQUENCE: 3

Met Ala Ser Arg Leu Leu Arg Gly Ala Gly Thr Leu Ala Ala Gln Ala
1               5                   10                  15

Leu Arg Ala Arg
            20

<210> SEQ ID NO 4
<211> LENGTH: 19
<212> TYPE: PRT
<213> ORGANISM: Homo sapiens

<400> SEQUENCE: 4

Met Ala Ser Arg Leu Leu Arg Gly Ala Gly Thr Leu Ala Ala Gln Ala
1               5                   10                  15

Leu Arg Ala

<210> SEQ ID NO 5
<211> LENGTH: 18
<212> TYPE: PRT
<213> ORGANISM: Homo sapiens

<400> SEQUENCE: 5

Met Ala Ser Arg Leu Leu Arg Gly Ala Gly Thr Leu Ala Ala Gln Ala
1               5                   10                  15

Leu Arg

<210> SEQ ID NO 6
<211> LENGTH: 20
<212> TYPE: PRT
<213> ORGANISM: Homo sapiens

<400> SEQUENCE: 6

Met Gly Gly Leu Trp Arg Pro Gly Trp Arg Cys Val Pro Phe Cys Gly
1               5                   10                  15

Trp Arg Trp Ile
            20

<210> SEQ ID NO 7
<211> LENGTH: 25
<212> TYPE: PRT
<213> ORGANISM: Homo sapiens

<400> SEQUENCE: 7

Met Ser Val Leu Thr Pro Leu Leu Leu Arg Gly Leu Thr Gly Ser Ala
1               5                   10                  15

```
Arg Arg Leu Pro Val Pro Arg Ala Lys
            20                  25

<210> SEQ ID NO 8
<211> LENGTH: 15
<212> TYPE: PRT
<213> ORGANISM: Homo sapiens

<400> SEQUENCE: 8

Met Leu Gly Gln Ser Ile Arg Arg Phe Thr Thr Ser Val Val Arg
1               5                   10                  15

<210> SEQ ID NO 9
<211> LENGTH: 24
<212> TYPE: PRT
<213> ORGANISM: Homo sapiens

<400> SEQUENCE: 9

Met Ala Val Val Gly Val Ser Ser Val Ser Arg Leu Leu Gly Arg Ser
1               5                   10                  15

Arg Pro Gln Leu Gly Arg Pro Met
            20

<210> SEQ ID NO 10
<211> LENGTH: 16
<212> TYPE: PRT
<213> ORGANISM: Homo sapiens

<400> SEQUENCE: 10

Met Leu Gly Gln Ser Ile Arg Arg Phe Thr Thr Ser Val Val Arg Arg
1               5                   10                  15

<210> SEQ ID NO 11
<211> LENGTH: 21
<212> TYPE: PRT
<213> ORGANISM: Homo sapiens

<400> SEQUENCE: 11

Met Gln Ala Leu Arg Val Ser Gln Ala Leu Ile Arg Ser Phe Ser Ser
1               5                   10                  15

Thr Ala Arg Asn Arg
            20

<210> SEQ ID NO 12
<211> LENGTH: 23
<212> TYPE: PRT
<213> ORGANISM: Homo sapiens

<400> SEQUENCE: 12

Met Leu Arg Asn Leu Leu Ala Leu Arg Gln Ile Gly Gln Arg Thr Ile
1               5                   10                  15

Ser Thr Ala Ser Arg Arg His
            20

<210> SEQ ID NO 13
<211> LENGTH: 12
<212> TYPE: PRT
<213> ORGANISM: Homo sapiens

<400> SEQUENCE: 13

Met Ala Leu Pro Leu Arg Pro Leu Thr Arg Gly Leu
1               5                   10
```

```
<210> SEQ ID NO 14
<211> LENGTH: 23
<212> TYPE: PRT
<213> ORGANISM: Homo sapiens

<400> SEQUENCE: 14

Met Ala Leu Pro Leu Arg Pro Leu Thr Arg Gly Leu Ala Ser Ala Ala
1               5                   10                  15

Lys Gly Gly His Gly Gly Ala
            20

<210> SEQ ID NO 15
<211> LENGTH: 24
<212> TYPE: PRT
<213> ORGANISM: Homo sapiens

<400> SEQUENCE: 15

Met Phe Pro Leu Val Lys Ser Ala Leu Asn Arg Leu Gln Val Arg Ser
1               5                   10                  15

Ile Gln Gln Thr Met Ala Arg Gln
            20

<210> SEQ ID NO 16
<211> LENGTH: 29
<212> TYPE: PRT
<213> ORGANISM: Homo sapiens

<400> SEQUENCE: 16

Met Pro Leu Leu Arg Gly Arg Cys Pro Ala Arg Arg His Tyr Arg Arg
1               5                   10                  15

Leu Ala Leu Leu Gly Leu Gln Pro Ala Pro Arg Phe Ala
            20                  25

<210> SEQ ID NO 17
<211> LENGTH: 21
<212> TYPE: PRT
<213> ORGANISM: Homo sapiens

<400> SEQUENCE: 17

Phe Thr Thr Phe Leu Thr Pro Ala Ala Tyr Val Leu Gly Asn Leu Lys
1               5                   10                  15

Gln Phe Arg Arg Asn
            20

<210> SEQ ID NO 18
<211> LENGTH: 22
<212> TYPE: PRT
<213> ORGANISM: Homo sapiens

<400> SEQUENCE: 18

Met Leu Ala Thr Arg Val Phe Ser Leu Val Gly Lys Arg Ala Ile Ser
1               5                   10                  15

Thr Ser Val Cys Val Arg
            20

<210> SEQ ID NO 19
<211> LENGTH: 23
<212> TYPE: PRT
<213> ORGANISM: Homo sapiens

<400> SEQUENCE: 19

Met Leu Trp Asn Leu Leu Ala Leu His Gln Ile Gly Gln Arg Thr Ile
```

-continued

```
1               5                   10                  15
Ser Thr Ala Ser His Arg His
                20

<210> SEQ ID NO 20
<211> LENGTH: 28
<212> TYPE: PRT
<213> ORGANISM: Homo sapiens

<400> SEQUENCE: 20

Met Arg Gly Ala Gly Pro Ser Pro Arg Gln Ser Pro Arg Thr Leu Arg
1               5                   10                  15

Pro Asp Pro Gly Pro Ala Met Ser Phe Phe Arg Arg
                20                  25

<210> SEQ ID NO 21
<211> LENGTH: 29
<212> TYPE: PRT
<213> ORGANISM: Homo sapiens

<400> SEQUENCE: 21

Met Ala Ile Gln Phe Arg Ser Leu Phe Pro Leu Ala Leu Pro Gly Met
1               5                   10                  15

Leu Ala Leu Leu Gly Trp Trp Trp Phe Phe Ser Arg Lys
                20                  25

<210> SEQ ID NO 22
<211> LENGTH: 27
<212> TYPE: PRT
<213> ORGANISM: Homo sapiens

<400> SEQUENCE: 22

Met Ala Ala Ala Ala Leu Gly Gln Ile Trp Ala Arg Lys Leu Leu Ser
1               5                   10                  15

Val Pro Trp Leu Leu Cys Gly Pro Arg Arg Tyr
                20                  25

<210> SEQ ID NO 23
<211> LENGTH: 30
<212> TYPE: PRT
<213> ORGANISM: Homo sapiens

<400> SEQUENCE: 23

Met Ala Ala Leu Leu Leu Arg His Val Gly Arg His Cys Leu Arg Ala
1               5                   10                  15

His Phe Ser Pro Gln Leu Cys Ile Arg Asn Ala Val Pro Leu
                20                  25                  30

<210> SEQ ID NO 24
<211> LENGTH: 26
<212> TYPE: PRT
<213> ORGANISM: Homo sapiens

<400> SEQUENCE: 24

Met Leu Arg Leu Pro Thr Val Phe Arg Gln Met Arg Pro Val Ser Arg
1               5                   10                  15

Val Leu Ala Pro His Leu Thr Arg Ala Tyr
                20                  25

<210> SEQ ID NO 25
<211> LENGTH: 24
<212> TYPE: PRT
```

<213> ORGANISM: Homo sapiens

<400> SEQUENCE: 25

Met Ala Leu Val His Lys Leu Leu Arg Gly Thr Tyr Phe Leu Arg Lys
1               5                   10                  15

Phe Ser Lys Pro Thr Ser Ala Leu
            20

<210> SEQ ID NO 26
<211> LENGTH: 28
<212> TYPE: PRT
<213> ORGANISM: Homo sapiens

<400> SEQUENCE: 26

Met Ala Ala Val Val Ala Leu Ser Leu Arg Arg Leu Pro Ala Thr
1               5                   10                  15

Thr Leu Gly Gly Ala Cys Leu Gln Ala Ser Arg Gly
            20                  25

<210> SEQ ID NO 27
<211> LENGTH: 28
<212> TYPE: PRT
<213> ORGANISM: Homo sapiens

<400> SEQUENCE: 27

Met Gln Arg Ala Val Ser Val Val Ala Arg Leu Gly Phe Arg Leu Gln
1               5                   10                  15

Ala Phe Pro Pro Ala Leu Cys Arg Pro Leu Ser Cys
            20                  25

<210> SEQ ID NO 28
<211> LENGTH: 27
<212> TYPE: PRT
<213> ORGANISM: Homo sapiens

<400> SEQUENCE: 28

Met Ala Ala Gln Cys Val Arg Leu Ala Arg Arg Ser Leu Pro Ala Leu
1               5                   10                  15

Ala Leu Ser Leu Arg Pro Ser Pro Arg Leu Leu
            20                  25

<210> SEQ ID NO 29
<211> LENGTH: 31
<212> TYPE: PRT
<213> ORGANISM: Homo sapiens

<400> SEQUENCE: 29

Met Ala Ala Pro Arg Ala Gly Arg Gly Ala Gly Trp Ser Leu Arg Ala
1               5                   10                  15

Trp Arg Ala Leu Gly Gly Ile Arg Trp Gly Arg Arg Pro Arg Leu
            20                  25                  30

<210> SEQ ID NO 30
<211> LENGTH: 25
<212> TYPE: PRT
<213> ORGANISM: Homo sapiens

<400> SEQUENCE: 30

Met Leu Ile Pro Phe Ser Met Lys Asn Cys Phe Gln Leu Leu Cys Asn
1               5                   10                  15

Cys Gln Val Pro Ala Ala Gly Phe Lys
            20                  25

<210> SEQ ID NO 31
<211> LENGTH: 30
<212> TYPE: PRT
<213> ORGANISM: Homo sapiens

<400> SEQUENCE: 31

Met Phe Pro Leu Val Lys Ser Ala Leu Asn Arg Leu Gln Val Arg Ser
1               5                   10                  15

Ile Gln Gln Thr Met Ala Arg Gln Ser His Gln Lys Arg Thr
            20                  25                  30

<210> SEQ ID NO 32
<211> LENGTH: 33
<212> TYPE: PRT
<213> ORGANISM: Homo sapiens

<400> SEQUENCE: 32

Met Leu Trp Asn Leu Leu Ala Leu His Gln Ile Gly Gln Arg Thr Ile
1               5                   10                  15

Ser Thr Ala Ser His Arg His Phe Lys Asn Lys Val Pro Glu Lys Gln
            20                  25                  30

Lys

<210> SEQ ID NO 33
<211> LENGTH: 34
<212> TYPE: PRT
<213> ORGANISM: Homo sapiens

<400> SEQUENCE: 33

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu Pro Pro Glu
            20                  25                  30

Gly Lys

<210> SEQ ID NO 34
<211> LENGTH: 34
<212> TYPE: PRT
<213> ORGANISM: Homo sapiens

<400> SEQUENCE: 34

Met Ala Ala Leu Lys Ala Leu Val Ser Gly Cys Gly Arg Leu Leu Arg
1               5                   10                  15

Gly Leu Leu Ala Gly Pro Ala Ala Thr Ser Trp Ser Arg Leu Pro Ala
            20                  25                  30

Arg Gly

<210> SEQ ID NO 35
<211> LENGTH: 20
<212> TYPE: PRT
<213> ORGANISM: Homo sapiens

<400> SEQUENCE: 35

Met Ser Val Val Arg Ser Ser Val His Ala Arg Trp Ile Val Gly Lys
1               5                   10                  15

Val Ile Gly Thr
            20

<210> SEQ ID NO 36

```
<211> LENGTH: 31
<212> TYPE: PRT
<213> ORGANISM: Homo sapiens

<400> SEQUENCE: 36

Met Leu Arg Ala Leu Ser Arg Leu Gly Ala Gly Thr Pro Cys Arg Pro
1               5                   10                  15

Arg Ala Pro Leu Val Leu Pro Ala Arg Gly Arg Lys Thr Arg His
            20                  25                  30

<210> SEQ ID NO 37
<211> LENGTH: 16
<212> TYPE: PRT
<213> ORGANISM: Homo sapiens

<400> SEQUENCE: 37

Met Phe Arg Arg Pro Val Leu Gln Val Leu Arg Gln Phe Val Arg His
1               5                   10                  15

<210> SEQ ID NO 38
<211> LENGTH: 13
<212> TYPE: PRT
<213> ORGANISM: Homo sapiens

<400> SEQUENCE: 38

Met Pro Ala Pro Arg Ala Pro Arg Ala Leu Ala Ala Ala
1               5                   10

<210> SEQ ID NO 39
<211> LENGTH: 34
<212> TYPE: PRT
<213> ORGANISM: Homo sapiens

<400> SEQUENCE: 39

Met Ala Ala Ser Val Val Cys Arg Ala Ala Thr Ala Gly Ala Gln Val
1               5                   10                  15

Leu Leu Arg Ala Arg Arg Ser Pro Ala Leu Leu Arg Thr Pro Ala Leu
            20                  25                  30

Arg Ser

<210> SEQ ID NO 40
<211> LENGTH: 14
<212> TYPE: PRT
<213> ORGANISM: Homo sapiens

<400> SEQUENCE: 40

Met Lys Leu Leu Thr Arg Ala Gly Ser Phe Ser Arg Phe Tyr
1               5                   10

<210> SEQ ID NO 41
<211> LENGTH: 13
<212> TYPE: PRT
<213> ORGANISM: Homo sapiens

<400> SEQUENCE: 41

Met Gly Leu Glu Asp Glu Gln Lys Met Leu Thr Glu Ser
1               5                   10

<210> SEQ ID NO 42
<211> LENGTH: 33
<212> TYPE: PRT
<213> ORGANISM: Homo sapiens

<400> SEQUENCE: 42
```

```
Met Glu Gly Leu Ala Val Arg Leu Leu Arg Gly Ser Arg Leu Leu Arg
1               5                   10                  15

Arg Asn Phe Leu Thr Cys Leu Ser Ser Trp Lys Ile Pro Pro His Val
            20                  25                  30

Ser

<210> SEQ ID NO 43
<211> LENGTH: 25
<212> TYPE: PRT
<213> ORGANISM: Homo sapiens

<400> SEQUENCE: 43

Met Phe Ser Arg Ala Gly Val Ala Gly Leu Ser Ala Trp Thr Leu Gln
1               5                   10                  15

Pro Gln Trp Ile Gln Val Arg Asn Met
            20                  25

<210> SEQ ID NO 44
<211> LENGTH: 24
<212> TYPE: PRT
<213> ORGANISM: Homo sapiens

<400> SEQUENCE: 44

Met Ala Ala Pro Ala Val Ser Gly Leu Ser Arg Gln Val Arg Cys Phe
1               5                   10                  15

Ser Thr Ser Val Val Arg Pro Phe
            20

<210> SEQ ID NO 45
<211> LENGTH: 24
<212> TYPE: PRT
<213> ORGANISM: Homo sapiens

<400> SEQUENCE: 45

Met Ala Ala Ala Leu Leu Ala Arg Ala Ser Gly Pro Ala Arg Arg Ala
1               5                   10                  15

Leu Cys Pro Arg Ala Trp Arg Gln
            20

<210> SEQ ID NO 46
<211> LENGTH: 22
<212> TYPE: PRT
<213> ORGANISM: Homo sapiens

<400> SEQUENCE: 46

Met Leu Pro Ala Ala Leu Leu Arg Arg Pro Gly Leu Gly Arg Leu Val
1               5                   10                  15

Arg His Ala Arg Ala Tyr
            20

<210> SEQ ID NO 47
<211> LENGTH: 24
<212> TYPE: PRT
<213> ORGANISM: Homo sapiens

<400> SEQUENCE: 47

Met Leu Ser Ala Leu Ala Arg Pro Val Ser Ala Ala Leu Arg Arg Ser
1               5                   10                  15

Phe Ser Thr Ser Ala Gln Asn Asn
            20
```

```
<210> SEQ ID NO 48
<211> LENGTH: 24
<212> TYPE: PRT
<213> ORGANISM: Homo sapiens

<400> SEQUENCE: 48

Met Phe Pro Leu Ala Arg Asn Ala Leu Ser Ser Leu Lys Ile Gln Ser
1               5                   10                  15

Ile Leu Gln Ser Met Ala Arg His
            20

<210> SEQ ID NO 49
<211> LENGTH: 24
<212> TYPE: PRT
<213> ORGANISM: Homo sapiens

<400> SEQUENCE: 49

Met Ala Leu Arg Ala Lys Ala Glu Val Cys Met Ala Val Pro Trp Leu
1               5                   10                  15

Ser Leu Gln Arg Ala Gln Ala Leu
            20

<210> SEQ ID NO 50
<211> LENGTH: 27
<212> TYPE: PRT
<213> ORGANISM: Homo sapiens

<400> SEQUENCE: 50

Met Ala Leu Leu Thr Ala Ala Ala Arg Leu Leu Gly Thr Lys Asn Ala
1               5                   10                  15

Ser Cys Leu Val Leu Ala Ala Arg His Ala Ser
            20                  25

<210> SEQ ID NO 51
<211> LENGTH: 25
<212> TYPE: PRT
<213> ORGANISM: Homo sapiens

<400> SEQUENCE: 51

Met Ala Ala Gly Phe Gly Arg Cys Cys Arg Val Leu Arg Ser Ile Ser
1               5                   10                  15

Arg Phe His Trp Arg Ser Gln His Thr
            20                  25

<210> SEQ ID NO 52
<211> LENGTH: 646
<212> TYPE: PRT
<213> ORGANISM: Homo sapiens

<400> SEQUENCE: 52

Met Ser Lys Gly Pro Ala Val Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Met Asn Pro Thr
        50                  55                  60

Asn Thr Val Phe Asp Ala Lys Arg Leu Ile Gly Arg Arg Phe Asp Asp
65                  70                  75                  80
```

-continued

```
Ala Val Val Gln Ser Asp Met Lys His Trp Pro Phe Met Val Val Asn
                 85                  90                  95

Asp Ala Gly Arg Pro Lys Val Gln Val Glu Tyr Lys Gly Glu Thr Lys
            100                 105                 110

Ser Phe Tyr Pro Glu Glu Val Ser Ser Met Val Leu Thr Lys Met Lys
        115                 120                 125

Glu Ile Ala Glu Ala Tyr Leu Gly Lys Thr Val Thr Asn Ala Val Val
    130                 135                 140

Thr Val Pro Ala Tyr Phe Asn Asp Ser Gln Arg Gln Ala Thr Lys Asp
145                 150                 155                 160

Ala Gly Thr Ile Ala Gly Leu Asn Val Leu Arg Ile Ile Asn Glu Pro
                165                 170                 175

Thr Ala Ala Ala Ile Ala Tyr Gly Leu Asp Lys Lys Val Gly Ala Glu
            180                 185                 190

Arg Asn Val Leu Ile Phe Asp Leu Gly Gly Gly Thr Phe Asp Val Ser
        195                 200                 205

Ile Leu Thr Ile Glu Asp Gly Ile Phe Glu Val Lys Ser Thr Ala Gly
    210                 215                 220

Asp Thr His Leu Gly Gly Glu Asp Phe Asp Asn Arg Met Val Asn His
225                 230                 235                 240

Phe Ile Ala Glu Phe Lys Arg Lys His Lys Lys Asp Ile Ser Glu Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Ile Glu Ile Asp Ser Leu Tyr
        275                 280                 285

Glu Gly Ile Asp Phe Tyr Thr Ser Ile Thr Arg Ala Arg Phe Glu Glu
    290                 295                 300

Leu Asn Ala Asp Leu Phe Arg Gly Thr Leu Asp Pro Val Glu Lys Ala
305                 310                 315                 320

Leu Arg Asp Ala Lys Leu Asp Lys Ser Gln Ile His Asp Ile Val Leu
                325                 330                 335

Val Gly Gly Ser Thr Arg Ile Pro Lys Ile Gln Lys Leu Leu Gln Asp
            340                 345                 350

Phe Phe Asn Gly Lys Glu Leu Asn Lys Ser Ile Asn Pro Asp Glu Ala
        355                 360                 365

Val Ala Tyr Gly Ala Ala Val Gln Ala Ala Ile Leu Ser Gly Asp Lys
    370                 375                 380

Ser Glu Asn Val Gln Asp Leu Leu Leu Leu Asp Val Thr Pro Leu Ser
385                 390                 395                 400

Leu Gly Ile Glu Thr Ala Gly Gly Val Met Thr Val Leu Ile Lys Arg
                405                 410                 415

Asn Thr Thr Ile Pro Thr Lys Gln Thr Gln Thr Phe Thr Thr Tyr Ser
            420                 425                 430

Asp Asn Gln Pro Gly Val Leu Ile Gln Val Tyr Glu Gly Glu Arg Ala
        435                 440                 445

Met Thr Lys Asp Asn Asn Leu Leu Gly Lys Phe Glu Leu Thr Gly Ile
    450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Ser Ala Val Asp Lys Ser Thr Gly
                485                 490                 495

Lys Glu Asn Lys Ile Thr Ile Thr Asn Asp Lys Gly Arg Leu Ser Lys
```

-continued

```
                500                 505                 510
Glu Asp Ile Glu Arg Met Val Gln Glu Ala Glu Lys Tyr Lys Ala Glu
        515                 520                 525

Asp Glu Lys Gln Arg Asp Lys Val Ser Ser Lys Asn Ser Leu Glu Ser
        530                 535                 540

Tyr Ala Phe Asn Met Lys Ala Thr Val Glu Asp Glu Lys Leu Gln Gly
545                 550                 555                 560

Lys Ile Asn Asp Glu Asp Lys Gln Lys Ile Leu Asp Lys Cys Asn Glu
                565                 570                 575

Ile Ile Asn Trp Leu Asp Lys Asn Gln Thr Ala Glu Lys Glu Glu Phe
                580                 585                 590

Glu His Gln Gln Lys Glu Leu Glu Lys Val Cys Asn Pro Ile Ile Thr
                595                 600                 605

Lys Leu Tyr Gln Ser Ala Gly Gly Met Pro Gly Gly Met Pro Gly Gly
        610                 615                 620

Phe Pro Gly Gly Gly Ala Pro Pro Ser Gly Gly Ala Ser Ser Gly Pro
625                 630                 635                 640

Thr Ile Glu Glu Val Asp
                645
```